US010961425B2

(12) United States Patent
Yoshida et al.

(10) Patent No.: US 10,961,425 B2
(45) Date of Patent: Mar. 30, 2021

(54) VISCOUS WATER-BASED COMPOSITION

(71) Applicant: KAO CORPORATION, Tokyo (JP)

(72) Inventors: Yutaka Yoshida, Wakayama (JP);
Yoshiaki Kumamoto, Wakayama (JP)

(73) Assignee: KAO CORPORATION, Tokyo (JP)

( * ) Notice: Subject to any disclaimer, the term of this patent is extended or adjusted under 35 U.S.C. 154(b) by 0 days.

(21) Appl. No.: 15/561,454

(22) PCT Filed: Mar. 8, 2016

(86) PCT No.: PCT/JP2016/057077
§ 371 (c)(1),
(2) Date: Sep. 25, 2017

(87) PCT Pub. No.: WO2016/152491
PCT Pub. Date: Sep. 29, 2016

(65) Prior Publication Data
US 2018/0118991 A1 May 3, 2018

(30) Foreign Application Priority Data
Mar. 26, 2015 (JP) .............................. JP2015-064319

(51) Int. Cl.
C09K 8/80 (2006.01)
C09K 8/70 (2006.01)
C09K 8/10 (2006.01)
E21B 43/267 (2006.01)
A61Q 19/00 (2006.01)
C08K 5/16 (2006.01)
A61L 9/01 (2006.01)
C08L 1/04 (2006.01)
A61K 8/73 (2006.01)
A61K 8/02 (2006.01)
C09K 8/40 (2006.01)
C09K 8/588 (2006.01)
C09K 8/90 (2006.01)
C09K 8/92 (2006.01)
E21B 21/00 (2006.01)
E21B 43/20 (2006.01)
E21B 43/25 (2006.01)
A61Q 5/02 (2006.01)
A61Q 5/10 (2006.01)
A61Q 1/06 (2006.01)

(52) U.S. Cl.
CPC ............... C09K 8/10 (2013.01); A61K 8/027 (2013.01); A61K 8/731 (2013.01); A61L 9/01 (2013.01); A61Q 19/00 (2013.01); C08K 5/16 (2013.01); C08L 1/04 (2013.01); C09K 8/40 (2013.01); C09K 8/588 (2013.01); C09K 8/90 (2013.01); C09K 8/92 (2013.01); E21B 21/00 (2013.01); E21B 43/20 (2013.01); E21B 43/25 (2013.01); A61K 2800/10 (2013.01); A61K 2800/262 (2013.01); A61K 2800/412 (2013.01); A61Q 1/06 (2013.01); A61Q 5/02 (2013.01); A61Q 5/10 (2013.01); C09K 2208/08 (2013.01)

(58) Field of Classification Search
None
See application file for complete search history.

(56) References Cited

U.S. PATENT DOCUMENTS

| 6,348,436 B1 | 2/2002 | Langlois et al. |
| 2006/0199742 A1 | 9/2006 | Arisz et al. |
| 2007/0196401 A1 | 8/2007 | Naruse et al. |
| 2012/0000392 A1 | 1/2012 | Mukai et al. |

(Continued)

FOREIGN PATENT DOCUMENTS

| CA | 2 921 219 A1 | 3/2015 |
| JP | 2008-536959 A | 9/2008 |

(Continued)

OTHER PUBLICATIONS

Extended European Search Report dated Oct. 5, 2018 for Application No. 16768394.5.
Japanese Office Action, dated Oct. 1, 2019, for Japanese Application No. 2016-044115.
International Search Report (Form PCT/ISA/210), dated Jun. 14, 2016, for International Application No. PCT/JP2016/057077.
Japanese Office Action for Japanese Application No. 2016-044115, dated Aug. 28, 2020.

Primary Examiner — Jeffrey D Washville
(74) Attorney, Agent, or Firm — Birch, Stewart, Kolasch & Birch, LLP

(57) ABSTRACT

A water-based composition containing: (A) fine cellulose fibers having a number-average fiber diameter of 0.5 nm or more and 200 nm or less, and having a carboxy group content of 0.1 mmol/g or more, wherein the carboxy group forms a salt with an alkali metal; and (B) an additive containing one or more compounds having carbon atoms and nitrogen atom or atoms, wherein a ratio thereof per molecule of the compound (number of carbon atoms/number of nitrogen atoms) is 3 or more and 45 or less, wherein the content of the component (A) is 0.2% by mass or more and 10% by mass or less, and wherein the content of the component (B) is 3 parts by mass or more and 150 parts by mass or less, based on 100 parts by mass of the component (A), and wherein the water-based composition has a viscosity at 80° C. at a rotational speed of 30 rpm of 80 mPa·s or more. Since the fine cellulose fibers or a salt composite thereof of the present invention retains a high viscosity even under high temperatures, the fine cellulose fibers or a salt composite thereof can be suitably used in various industrial applications represented by thickening agents during gas and oil drilling, cosmetic applications, and other applications requiring manufactured article stability at high temperatures.

18 Claims, No Drawings

(56) References Cited

U.S. PATENT DOCUMENTS

| | | | |
|---|---|---|---|
| 2012/0283363 A1 | 11/2012 | Kumamoto et al. | |
| 2012/0308624 A1 | 12/2012 | Isogai et al. | |
| 2013/0035263 A1* | 2/2013 | Laukkanen | C09K 8/40 507/112 |
| 2015/0107832 A1* | 4/2015 | DeWolf | C09K 8/52 166/266 |
| 2016/0032168 A1 | 2/2016 | Al-Bagoury et al. | |
| 2016/0200958 A1 | 7/2016 | Goi et al. | |
| 2016/0200964 A1* | 7/2016 | Goi | C08B 15/02 428/401 |
| 2017/0226398 A1* | 8/2017 | Shimaoka | C09K 8/10 |

FOREIGN PATENT DOCUMENTS

| | | |
|---|---|---|
| JP | 2010-37348 A | 2/2010 |
| JP | 2010-202856 A | 9/2010 |
| JP | 2011-47084 A | 3/2011 |
| JP | 2011-140738 A | 7/2011 |
| JP | 2012-81533 A | 4/2012 |
| JP | 2012-126786 A | 7/2012 |
| JP | 2012-126788 A | 7/2012 |
| JP | 2014-105114 A | 6/2014 |
| JP | 2016-65116 A | 4/2016 |
| WO | WO 2011/071156 A1 | 6/2011 |
| WO | WO 2011/089323 A1 | 7/2011 |
| WO | WO 2011/089709 A1 | 7/2011 |
| WO | WO 2014/148917 A1 | 9/2014 |

* cited by examiner

VISCOUS WATER-BASED COMPOSITION

FIELD OF THE INVENTION

The present invention relates to a viscous water-based composition. More specifically, the present invention relates to a viscous water-based composition which can be suitably used in various industrial applications represented by a thickening agent used in piling construction and underground extraction of petroleum or the like, cosmetic applications, and other applications that require stability in the manufactured articles at a high temperature.

BACKGROUND OF THE INVENTION

Conventionally, polymeric materials have been used in order to maintain thickening property and dispersion stability. The polymeric materials include, for example, water-soluble cellulose derivatives such as methyl cellulose and carboxymethyl cellulose salts; synthetic polymers such as polyvinyl alcohol, polyvinyl pyrrolidone, carboxyvinyl polymers, and polyethylene glycols; natural macromolecular polysaccharides such as quince seed, VEEGUM, xanthan gum, and hyaluronates; and the like. Among them, the cellulose fibers are abundant in nature, and have excellent biodegradability, so that the cellulose fibers are expected to be microfibrillated and applied in a wide range of fields.

For example, Patent Publication 1 discloses a viscous composition prepared by mixing fine cellulose fibers in which a C6-position hydroxyl group of a glucose unit in the cellulose molecule is oxidized to be modified to an aldehyde group and a carboxy group, with water is utilized in cosmetic base materials and toiletry article base materials. Since the above fine cellulose fibers in Examples are oxidized and then reacted with sodium hydroxide, it is suggested that a sodium salt is formed with the aldehyde group and the carboxy group.

Patent Publication 2 discloses that fine cellulose fibers in which a C6-position hydroxyl group of a glucose unit in a cellulose molecule is modified to a carboxy group, and the carboxy group is in the form of a salt of monoamines, are used in applications similar to those of Patent Publication 1.

In addition, in the oil fields producing petroleum and natural gases, it has been tried to use fine cellulose fibers. In the field of art, conventionally, a polymeric material as mentioned above has been used as a viscosity conditioner when drilling and drawing are carried out to form a film on a wall surface of a drilled hole to stabilize or the polymeric material is injected to an underground layer for improving productivity to allow swelling thereof, thereby forming artificial fractures. However, Patent Publication 3 discloses that a dispersion of fine cellulose fibers in water has been used in a drilling fluid, a fracturing liquid, a distribution fluid, or the like.

Patent Publication 1: WO 2011/089709
Patent Publication 2: Japanese Patent Laid-Open No. 2012-126786
Patent Publication 3: WO 2011/089323

SUMMARY OF THE INVENTION

The present invention relates to the following [1] to [7]:
[1] A water-based composition containing:
  (A) fine cellulose fibers having a number-average fiber diameter of 0.5 nm or more and 200 nm or less, and having a carboxy group content of 0.1 mmol/g or more, wherein the carboxy group forms a salt with an alkali metal; and
  (B) an additive containing one or more compounds having carbon atoms and nitrogen atom or atoms, wherein a ratio thereof per molecule of the compound (number of carbon atoms/number of nitrogen atoms) is 3 or more and 45 or less,
  wherein the content of the above component (A) is 0.2% by mass or more and 10% by mass or less, and wherein the content of the above component (B) is 3 parts by mass or more and 150 parts by mass or less, based on 100 parts by mass of the component (A), and wherein the water-based composition has a viscosity at 80° C. at a rotational speed of 30 rpm of 80 mPa·s or more.
[2] Use of a water-based composition as defined in the above [1] as cosmetics selected from cream, milky lotion, and lipstick.
[3] Use of a water-based composition as defined in the above [1] as a household article selected from aromatics, shampoos, and hairdyes.
[4] Use of a water-based composition as defined in the above [1] as industrially manufactured articles selected from blowing agents, paints, and concrete.
[5] Use of a water-based composition as defined in the above [1] as any one of fluids selected from the group consisting of drilling fluids, spacer fluids, injection fluids for well stimulations, and displacement fluids for enhanced oil recovery, which are usable during piling construction, extraction of petroleum, or well drilling of oil fields.
[6] A method for treating an underground layer characterized in that the method includes treating an underground layer with a water-based composition as defined in the above [1].
[7] A method for recovering earth and sand or rocks generated by drilling, including feeding a water-based composition as defined in the above [1] to a tip end of an underground drilling hole, and recovering earth and sand or rocks generated by drilling aboveground.

DETAILED DESCRIPTION OF THE INVENTION

Although it has been tried to apply fine cellulose fibers to applications that require thickening effects, the present inventors have studied and found that water-based compositions containing fine cellulose fibers also show the lowering in viscosity at a high temperature in the same manner as in conventional thickening agents, whereby suggesting the need of further improvements thereof.

The present invention relates to a water-based composition containing fine cellulose fibers in which the lowering in viscosity at a high temperature is controlled.

The water-based composition of the present invention exhibits some excellent effects of having excellent operability because the water-based composition also has excellent thixotropy while showing a high viscosity even at a high-temperature.

The water-based composition of fine cellulose fibers shows excellent viscosity but its viscosity at a high temperature is lowered in the same manner as in a conventional thickening agent, so that further improvements are needed. In view of the above, as a result of studies, the present inventors have surprisingly found that the lowering in viscosity at a high temperature is controlled and the thixotropy becomes excellent by combining a nitrogen-containing hydrocarbon compound having a specified ratio of carbon atoms to nitrogen atom or atoms, with specified fine cellulose fibers. Although the detailed reasons are unclear, it is assumed that the addition of a compound having a particular atomic composition makes it possible to form an apparent crosslinking structure between the fine cellulose fibers that is relatively firm and recombinable is formed by adding a compound having a specified atomic composition, but the present invention is by no means limited by these assumptions. As to the lowering in viscosity as used herein, it can be evaluated that when a proportion of a viscosity at a high temperature to the viscosity at an ambient temperature is examined, the smaller the value, the larger the lowering in its viscosity at a high temperature, and, for example, the proportion can be expressed as a ratio of a viscosity at 80° C. to a viscosity at 25° C. (viscosity at 80° C./viscosity at 25° C.).

The water-based composition of the present invention contains particular fine cellulose fibers and a particular additive.

[Water-Based Composition]
[(A) Fine Cellulose Fibers]

The fine cellulose fibers usable in the present invention are not particularly limited, so long as the fine cellulose fibers have a specified number-average fiber diameter and a specified carboxy group content, in which the carboxy group forms a salt with an alkali metal.

(Number-Average Fiber Diameter)

The fine cellulose fibers in the present invention have a number-average fiber diameter of 0.5 nm or more and 200 nm or less, and the fine cellulose fibers have a number-average fiber diameter of preferably 0.8 nm or more, and more preferably 1.0 nm or more, from the viewpoint of having crystalline property, thereby maintaining thermal stability. In addition, the fine cellulose fibers have a number-average fiber diameter of preferably 100 nm or less, more preferably 50 nm or less, even more preferably 20 nm or less, even more preferably 10 nm or less, and still even more preferably 5 nm or less, from the viewpoint of exhibiting structural viscosity by providing a microfine structure. Here, the number-average fiber diameter of the cellulose fibers as used herein can be measured with an atomic force microscope (AFM), which is specifically measured by the method described in Examples set forth below. Generally, a minimum unit of cellulose nanofibers prepared from higher plants is packed in nearly square form having sizes of 6×6 molecular chains, so that the height analyzed in the image according to the AFM can be assumed to be a width of the fibers.

(Carboxy Group Content)

The fine cellulose fibers in the present invention have a carboxy group content of 0.1 mmol/g or more, and the fine cellulose fibers have a carboxy group content of preferably 0.4 mmol/g or more, more preferably 0.6 mmol/g or more, and even more preferably 0.8 mmol/g or more, from the viewpoint of stability and thickening effects in the water-based composition. In addition, the fine cellulose fibers have a carboxy group content of preferably 3.0 mmol/g or less, more preferably 2.7 mmol/g or less, even more preferably 2.5 mmol/g or less, and still even more preferably 2.0 mmol/g or less, from the viewpoint of handling properties and costs. The fine cellulose fibers usable in the present invention may unintentionally contain fine cellulose fibers of which carboxy group content is outside the range as impurities. Here, the term "carboxy group content" means a total amount of carboxy groups in the cellulose constituting the fine cellulose fibers, which is specifically measured by the method described in Examples set forth below.

(Modification of Carboxy Group)

In the fine cellulose fibers in the present invention, the above carboxy group forms a salt with an alkali metal. Here, in the present specification, the carboxy group of the fine cellulose fibers forming a salt with an alkali metal means a state in which an alkali metal is directly ionically bonded to a carboxy group on the surface of the fine cellulose fibers. Having this state, the fine cellulose fibers exhibit some effects of high water dispersibility and structural viscosity. The alkali metal is preferably Li, Na, K, or Rb, more preferably Na or K, and even more preferably Na, from the viewpoint of costs.

The introduction of the above alkali metal is obtained by carrying out an oxidation treatment of a reaction system as an alkaline region when the carboxy group is present on the surface of fine cellulose fibers. The usable alkali includes alkali metal hydroxides such as sodium hydroxide, potassium hydroxide, and lithium hydroxide. Among them, sodium hydroxide or potassium hydroxide is preferred, and sodium hydroxide is more preferred, from the viewpoint of costs. Here, the method of oxidization treatment will be described later.

(Average Aspect Ratio)

In addition, the fine cellulose fibers in the present invention have an average aspect ratio (fiber length/fiber diameter) of preferably 10 or more, more preferably 20 or more, even more preferably 50 or more, still even more preferably 100 or more, and still even more preferably 200 or more, from the viewpoint of exhibiting structural viscosity. In addition, the fine cellulose fibers have an average aspect ratio of preferably 1,000 or less, more preferably 500 or less, even more preferably 400 or less, and still even more preferably 350 or less, from the viewpoint of costs and handling property. Here, the average aspect ratio as used herein is obtained by taking an inverse of the aspect ratio of the cellulose fibers according to the following formula (1), from the relationship between a cellulose fiber concentration in the dispersion and a specific viscosity against water of the dispersion. Here, the following formula (1) is derived from viscosity equation (8.138) of a rigid rod-shape molecule described in *The Theory of Polymer Dynamics*, M. DOI and D. F. EDWARDS, CLARENDON PRESS•OXFORD, 1986, P312 and a relation of $Lb^2 \times \rho = M/N_A$, wherein L is a fiber length, b is a fiber width (assuming that a cross section of the cellulose fibers is a square), p is a concentration of the cellulose fibers (kg/m$^3$), M is a molecular weight, and $N_A$ is an Avogadro number. In addition, in the above viscosity formula (8.138), the rigid rod-shaped molecule is assumed as cellulose fibers. In the following formula (1), $\eta_{SP}$ is a specific viscosity, $\pi$ is a ratio of the circumference to a diameter, ln is a natural logarithm, P is an aspect ratio (L/b), $\gamma$=0.8, $\rho_S$ is a density of a dispersion medium (kg/m$^3$), $\rho_0$ is a density of cellulose crystals (kg/m$^3$), and C is a mass concentration of cellulose (C=$\rho/\rho_S$).

$$\eta_{sp} = \frac{2\pi P^2}{45(\ln P - \gamma)} \times \frac{\rho_s}{\rho_0} \times C \tag{1}$$

(Crystallinity)

The fine cellulose fibers have a crystallinity of preferably 30% or more, more preferably 35% or more, even more preferably 40% or more, and still even more preferably 45% or more, from the viewpoint of exhibiting viscosity at a high temperature. In addition, the fine cellulose fibers have a crystallinity of preferably 95% or less, more preferably 90% or less, even more preferably 85% or less, and still even more preferably 80% or less, from the viewpoint of costs of the cellulose raw materials used. The crystallinity of the cellulose as used herein is a cellulose I crystallinity calculated according to Segal method from diffraction intensity values according to X-ray diffraction method, which is defined by the following calculation formula (A):

$$\text{Cellulose } I \text{ Crystallinity (\%)} = [(I22.6 - I18.5)/I22.6] \times 100 \quad (A)$$

wherein I22.6 is a diffraction intensity of a lattice face (face 002) (angle of diffraction 2θ=22.6°), and I18.5 is a diffraction intensity of an amorphous portion (angle of diffraction 2θ=18.5°), in X-ray diffraction.

Here, cellulose I is a crystalline form of a natural cellulose, and the cellulose I crystallinity means a proportion of the amount of crystalline region that occupies the entire cellulose.

<Production Method>

The fine cellulose fibers usable in the present invention can be produced in accordance with a known method without particular limitations. For example, a reaction of introducing an alkali metal to previously prepared fine cellulose fibers may be carried out, or a reaction of introducing an alkali metal during the preparation of fine cellulose fibers may be carried out. Here, fine cellulose fibers can be produced according to a known method, for example, a method described in Japanese Patent Laid-Open No. 2011-140632.

Specifically, the fine cellulose fibers can be obtained by, for example, a method including oxidizing natural cellulose fibers in the presence of an N-oxyl compound, to provide an alkali metal salt form of carboxy group-containing cellulose fibers (oxidization treatment step); and subjecting the resulting fibers to finely pulverizing treatment (finely pulverizing step).

(Oxidization Treatment Step)

First, a slurry of natural cellulose fibers dispersed in water is prepared. The slurry is obtained by adding water in an amount of about 10 to about 1,000 times the amount on mass basis based on the raw material natural cellulose fibers (on absolute dry basis: the mass of natural cellulose fibers after subjection to thermal drying at 150° C. for 30 minutes), and treating the mixture with a mixer or the like. The natural cellulose fibers include, for example, wooden pulp such as pulp from needle-leaf trees and pulp from broad-leaf trees; cotton pulp such as cotton linter and cotton lint; non-wooden pulp such as maize straw pulp and bagasse pulp; bacteria cellulose; and the like. These natural cellulose fibers can be used alone or in a combination of two or more kinds. The natural cellulose fibers may be subjected to a treatment of increasing surface areas such as treatment with a beater. In addition, the cellulose I crystallinity of the above-mentioned commercially available pulp is usually 80% or more.

Next, the above-mentioned natural cellulose fibers are subjected to an oxidation treatment in the presence of an N-oxyl compound to provide carboxy group-containing cellulose fibers, which may be hereinafter simply referred to as "oxidization treatment."

As the N-oxyl compound, one or more heterocyclic N-oxyl compounds selected from piperidinoxyl compounds, pyrrolidinoxyl compounds, imidazolinoxyl compounds, and azaadamantane compounds each having an alkyl group having 1 or 2 carbon atoms are preferred. Among them, the piperidinoxyl compounds having an alkyl group having 1 or 2 carbon atoms are preferred, from the viewpoint of reactivity, which includes di-tert-alkylnitroxyl compounds such as a 2,2,6,6-tetraalkylpiperidin-1-oxyl (TEMPO), a 4-hydroxy-2,2,6,6-tetraalkylpiperidin-1-oxyl, a 4-alkoxy-2,2,6,6-tetraalkylpiperidin-1-oxyl, a 4-benzoyloxy-2,2,6,6-tetraalkylpiperidin-1-oxyl, a 4-amino-2,2,6,6-tetraalkylpiperidin-1-oxyl; a 4-acetamide-TEMPO, a 4-carboxy-TEMPO, a 4-phosphonoxy-TEMPO, and the like. Among these piperidinoxyl compounds, a 2,2,6,6-tetramethylpiperidin-1-oxyl (TEMPO), a 4-hydroxy-2,2,6,6-tetramethylpiperidin-1-oxyl, and a 4-methoxy-2,2,6,6-tetramethylpiperidin-1-oxyl are more preferred, and a 2,2,6,6-tetramethylpiperidin-1-oxyl (TEMPO) is even more preferred.

The amount of the N-oxyl compound may be a catalytic amount, and the amount is preferably from 0.001 to 10% by mass, more preferably from 0.01 to 9% by mass, even more preferably from 0.1 to 8% by mass, and still even more preferably from 0.5 to 5% by mass, based on the natural cellulose fibers, on absolute dry basis.

In the oxidation treatment of the natural cellulose fibers, an oxidizing agent can be used. The oxidizing agent includes oxygen or the air and peroxides; halogens, hypohalous acids, halous acids, perhalo acid, and alkali metal salts or alkaline earth metal salts thereof, halogen oxides, nitrogen oxide, and the like, from the viewpoint of solubility, reaction rate or the like when a solvent is adjusted to an alkaline region. Among them, an alkali metal hypohalite is preferred, which is specifically exemplified by sodium hypochlorite and sodium hypobromite. The amount of the oxidizing agent used may be selected in accordance with the carboxy group substitution degree (oxidation degree) of the natural cellulose fibers, and the amount of the oxidizing agent used is not unconditionally determined because the yields of the oxidation reaction differ depending upon the reaction conditions. The amount is within the range of preferably from about 1 to about 100% by mass, based on the raw material natural cellulose fibers, on absolute dry basis.

In addition, in order to even more efficiently carry out the oxidation reaction, a bromide such as sodium bromide or potassium bromide, or an iodide such as sodium iodide or potassium iodide can be used as a promoter. The amount of the promoter may be an effective amount that can exhibit its function, without particular limitations.

The reaction temperature in the oxidation treatment is preferably 50° C. or lower, more preferably 40° C. or lower, and even more preferably 20° C. or lower, from the viewpoint of selectivity of the reaction and suppression of side reaction, and the lower limit of the reaction temperature is preferably −5° C. or higher.

In addition, from the viewpoint that a pH of the reaction system matches with the property of the oxidizing agent, in the present invention, a reaction system can be adjusted to an alkaline region with an alkali metal hydroxide such as sodium hydroxide, potassium hydroxide or lithium hydroxide, preferably with sodium hydroxide or potassium hydroxide, and more preferably with sodium hydroxide, from the viewpoint of costs. Specifically, for example, when sodium hypochlorite is used as an oxidizing agent, a pH of the reaction system is preferably on an alkaline side with sodium hydroxide, preferably a pH of from 7 to 13, and more preferably a pH of from 10 to 13. Also, it is desired that a reaction time is from 1 to 240 minutes.

By carrying out the above-mentioned oxidation treatment, carboxy group-containing cellulose fibers having a carboxy group content of 0.1 mmol/g or more, in which the carboxy group is in the form of an alkali metal salt, are obtained.

(Purifying Step)

The carboxy group-containing cellulose fibers obtainable by the above-mentioned oxidation reaction contain an N-oxyl compound such as TEMPO used as a catalyst, or a by-product salt. The carboxy group-containing cellulose fibers may be subjected to the subsequent steps without any treatments, or the carboxy group-containing cellulose fibers may be subjected to purification, whereby carboxy group-containing cellulose fibers having a high purity can be obtained. As a purification method, an optimal method can be employed according to the kinds of the solvents in the oxidation reaction, the degree of oxidation of the product, and the degree of purification. For example, the purification method includes re-precipitation with a highly dissolvable solvent water and a hardly dissolvable solvent such as methanol, ethanol, or acetone, extraction of TEMPO or the like to a solvent that allows phase separation with water, such as hexane, and other purifications with dialysis or the like.

(Finely Pulverizing Step)

After the above-mentioned purifying step, a step of finely pulverizing the carboxy group-containing cellulose fibers obtained is carried out. In the finely pulverizing step, it is preferable that the carboxy group-containing cellulose fibers obtained through the above-mentioned purifying step are dispersed in a solvent, and subjected to a finely pulverizing treatment. By carrying out this finely pulverizing step, fine cellulose fibers having a number-average fiber diameter and an average aspect ratio respectively within the ranges mentioned above are obtained.

The solvent used as a dispersion medium is exemplified by water, an alcohol having from 1 to 6 carbon atoms, and preferably from 1 to 3 carbon atoms, such as methanol, ethanol, or propanol; a ketone having from 3 to 6 carbon atoms, such as acetone, methyl ethyl ketone or methyl isobutyl ketone; a linear or branched saturated hydrocarbon or unsaturated hydrocarbon having from 1 to 6 carbon atoms; an aromatic hydrocarbon such as benzene or toluene; a halogenated hydrocarbon such as methylene chloride or chloroform; a lower alkyl ether having from 2 to 5 carbon atoms; a polar solvent such as N,N-dimethylformamide, N,N-dimethylacetamide, dimethyl sulfoxide, and a diester obtained from succinic acid and triethylene glycol monomethyl ether, and the like. These solvents can be used alone or in a mixture of two or more kinds. The solvent is preferably water, an alcohol having from 1 to 6 carbon atoms, a ketone having from 3 to 6 carbon atoms, a lower alkyl ether having from 2 to 5 carbon atoms, or a polar solvent such as N,N-dimethylformamide, N,N-dimethylacetamide, dimethyl sulfoxide, or methyl triglycol succinate diester, from the viewpoint of operability of the finely pulverizing treatment, and more preferably water, from the viewpoint of environmental friendliness. The amount of the solvent used may be an effective amount that can disperse the carboxy group-containing cellulose fibers, without particular limitations. The solvent is used in an amount of preferably from 1 to 500 times the mass, and more preferably from 2 to 200 times the mass, based on the carboxy group-containing cellulose fibers.

In addition, as an apparatus to be used in the finely pulverizing treatment, a known dispersing machine is suitably used. For example, a disintegrator, a beating machine, a low-pressure homogenizer, a high-pressure homogenizer, a grinder, a cutter mill, a ball-mill, a jet mill, a short shaft extruder, a twin-screw extruder, an ultrasonic agitator, a juice mixer for households, or the like can be used. In addition, the solid content concentration of the reaction product fibers in the finely pulverizing treatment is preferably 50% by mass or less, from the viewpoint of handling property.

The form of the carboxy group-containing fine cellulose fibers obtainable after the finely pulverizing step can also be, as occasion demands, in the form of a suspension of which solid content concentration is adjusted, e.g. visually colorless transparent or opaque liquid, or in the form of powder subjected to a drying treatment, provided that it is intended to mean that the fine cellulose fibers are in the form of an aggregated powder, not cellulose particles. Here, when provided in the form of a suspension, as a dispersion medium, water alone may be used, or a mixed solvent of water with other organic solvent, e.g. an alcohol such as ethanol, a surfactant, an acid, a base or the like may be used.

By subjecting the natural cellulose fibers to the oxidation treatment and the finely pulverizing treatment as described above, hydroxyl groups at a C6-position of the cellulose constituting unit are selectively oxidized to carboxy groups via aldehyde groups, and cellulose fibers being finely pulverized to a number-average fiber diameter of 0.5 nm or more and 200 nm or less, and having a crystallinity of preferably 30% or more, the cellulose fibers being composed of cellulose having the above-mentioned carboxy group content of 0.1 mmol/g or more, can be obtained. Here, the above-mentioned carboxy group-containing fine cellulose fibers have a cellulose I crystal structure. This means that the carboxy group-containing fine cellulose fibers used in the present invention are fibers prepared by subjecting cellulose solid raw materials derived from nature having a cellulose I crystal structure to surface oxidation and finely pulverizing treatment.

[(B) Additives]

In the present invention, an additive containing one or more compounds having carbon atoms and nitrogen atom or atoms, wherein a ratio thereof per molecule of the compound (number of carbon atoms/number of nitrogen atoms) is 3 or more and 45 or less is used. By using the nitrogen-containing compound having the above ratio, the effects of forming a crosslinked structure that is relatively firm and recombinable between the fine cellulose fibers are exhibited.

As the compound having the above ratio, specifically, a quaternary ammonium salt, an amine, or an amide can be used.

(Quaternary Ammonium Salt)

The quaternary ammonium salt usable in the present invention is a quaternary ammonium salt having a ratio of carbon atoms to nitrogen atom or atoms per molecule of the compound (number of carbon atoms/number of nitrogen atoms) of 3 or more and 45 or less.

The quaternary ammonium has the above ratio of preferably 4 or more, more preferably 6 or more, and even more preferably 20 or more, from the viewpoint of a thickening aiding effect and thermal stability. In addition, the quaternary ammonium has the above ratio of preferably 40 or less, more preferably 35 or less, even more preferably 30 or less, and still even more preferably 25 or less, from the viewpoint of a thickening aiding effect and thermal stability, and water solubility.

The quaternary ammonium has the number of carbon atoms per molecule of the compound of preferably 4 or more, more preferably 6 or more, even more preferably 12 or more, and even more preferably 18 or more, from the viewpoint of exhibiting a thickening aiding effect and thermal stability. In addition the quaternary ammonium has the number of carbon atoms of preferably 45 or less, more preferably 35 or less, even more preferably 30 or less, and even more preferably 25 or less, from the viewpoint of water solubility.

The quaternary ammonium has the number of nitrogen atom or atoms per molecule of the compound of preferably 1 or more and 2 or less, and more preferably 1, from the viewpoint of exhibiting a thickening aiding effect and thermal stability.

The counterion of the quaternary ammonium is not particularly limited. For example, the counterion is preferably a halogen atom, more preferably Br, Cl, and I, and even more preferably Br and Cl, from the viewpoint of water solubility.

The quaternary ammonium salt has a molecular weight of preferably 70 or more, more preferably 100 or more, even more preferably 200 or more, even more preferably 300 or more, and still even more preferably 350 or more, from the viewpoint of exhibiting a thickening aiding effect and thermal stability, and the quaternary ammonium salt has a molecular weight of preferably 500 or less, and more preferably 400 or less, from the same viewpoint.

The quaternary ammonium salt compound includes a compound represented by the general formula (1):

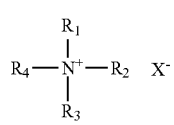

(1)

wherein each of $R_1$, $R_2$, $R_3$, and $R_4$, which may be identical or different, is an alkyl group having from 1 to 20 carbon atoms, an aryl group having from 6 to 20 carbon atoms, or an aralkyl group having from 7 to 20 carbon atoms; and X is F, Br, Cl, or I.

The alkyl group in the general formula (1) has the number of carbon atoms of preferably from 1 to 20, more preferably from 5 to 18, and even more preferably from 8 to 16. Specific examples include a methyl group, an ethyl group, a propyl group, an isopropyl group, a butyl group, an isobutyl group, a sec-butyl group, a tert-butyl group, a pentyl group, an isopentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an eicosyl group, and groups in which these groups are substituted with a substituent given later. Any of them can be used so long as a total number of carbon atoms for $R_1$, $R_2$, $R_3$, and $R_4$ is within the above range.

The aryl group in the general formula (1) has the number of carbon atoms of preferably from 6 to 20, more preferably from 6 to 14, and even more preferably from 6 to 10. Specific examples include a phenyl group, a naphthyl group, an anthryl group, a phenanthryl group, a biphenyl group, and groups in which these groups are substituted with a substituent given later.

The aralkyl group in the general formula (1) has the number of carbon atoms of preferably from 7 to 20, more preferably from 7 to 14, and even more preferably from 7 to 10. Specific examples of the aralkyl group include a benzyl group, a phenetyl group, a phenylpropyl group, a phenylpentyl group, a phenylhexyl group, a phenylheptyl group, a phenyloctyl group, and groups in which an aromatic group of these groups is substituted with a substituent given later.

The above substituent is preferably a group in which a total number of carbon atoms of all the function groups including the substituent falls within the above range. The substituent includes, for example, alkyl groups having from 1 to 6 carbon atoms, such as a methyl group, an ethyl group, a propyl group, an isopropyl group, a butyl group, an isobutyl group, a sec-butyl group, a tert-butyl group, a pentyl group, an isopentyl group, and a hexyl group; alkoxy groups having from 1 to 6 carbon atoms, such as a methoxy group, an ethoxy group, a propoxy group, an isopropoxy group, a butoxy group, an isobutoxy group, a sec-butoxy group, a tert-butoxy group, a pentyloxy group, an isopentyloxy group, and a hexyloxy group; alkoxycarbonyl groups of which alkoxy group has from 1 to 6 carbon atoms, such as a methoxycarbonyl group, an ethoxycarbonyl group, a propoxycarbonyl group, an isopropoxycarbonyl group, a butoxycarbonyl group, an isobutoxycarbonyl group, a sec-butoxycarbonyl group, a tert-butoxycarbonyl group, a pentyloxycarbonyl group, and an isopentyloxycarbonyl group; halogen atoms such as a fluorine atom, a chlorine atom, a bromine atom, and an iodine atom; acyl groups having from 1 to 6 carbon atoms such as an acetyl group and a propionyl group; aralkyl groups; aralkyloxy groups; alkylamines having from 1 to 6 carbon atoms; and dialkylamino groups of which alkyl group has the number of carbon atoms of from 1 to 6. Here, the above aryl group or aralkyl group itself may be bound as a substituent.

So long as $R_1$, $R_2$, $R_3$, and $R_4$ in the general formula (1) have a total number of carbon atoms within the above range, each of them may be any of an alkyl group, an aryl group, or an aralkyl group mentioned above.

X in the general formula (1) includes F, Br, Cl, or I, preferably Br, Cl, or I, and more preferably Br or Cl.

Specific examples of the compound represented by the general formula (1) include tetramethylammonium halides, tetraethylammonium halides, tetrapropylammonium halides, tetrabutylammonium halides, tetrapentylammonium halides, tetrahexylammonium halides, tetraphenylammonium halides, tetrabenzylammonium halides, ethyltrimethylammonium halide, propyltrimethylammonium halides, butyltrimethylammonium halides, pentyltrimethylammonium halides, hexyltrimethylammonium halides, octyltrimethylammonium halides, decyltrimethylammonium halides, dodecyltrimethylammonium halides, tetradecyltrimethylammonium halides, hexadecyltrimethylammonium halides, octadecyltrimethylammonium halides, phenyltrimethylammonium halides, benzyltrimethylammonium halides, pentyltripropylammonium chloride, hexyltripropylammonium chloride, octyltripropylammonium chloride, decyltripropylammonium chloride, phenyltripropylammonium chloride, benzyltripropylammonium chloride, dioctyldimethylammonium halides, didecyldimethylammonium halides, didodecyldimethylammonium halides, dimyristyldimethylammonium halides, butylbenzyldimethylammonium chloride, pentylbenzyldimethylammonium chloride, hexylbenzyldimethylammonium chloride, octylbenzyldimethylammonium chloride, decylbenzyldimethylammonium chloride, dodecylbenzyldimethylammonium chloride, myristylbenzyldimethylammonium chloride, palmitylbenzyldimethylammonium chloride, and stearylbenzyldimethylammonium chloride.

These can be used alone or in a combination of two or more kinds, and those that are produced by known methods and commercially available products can be used.

In particular, from the viewpoint of exhibiting a thickening aiding effect and thermal stability, tetramethylammonium halides, tetraethylammonium halides, tetrapropylammonium halides, tetrabutylammonium halides, pentyltrimethylammonium halides, hexyltrimethylammonium halides, octyltrimethylammonium halides, decyltrimethylammonium halides, dodecyltrimethylammonium halides, tetradecyltrimethylammonium halides, hexadecyltrimethylammonium halides, octadecyltrimethylammonium halides, phenyltrimethylammonium halides, benzyltrimethylammonium halides, phenyltripropylammonium chloride, dioctyldimethylammonium halides, didecyldimethylammonium halides, didodecyldimethylammonium halides, dimyristyldimethylammonium halides, octylbenzyldimethylammonium chloride, decylbenzyldimethylammonium chloride, dodecylbenzyldimethylammonium chloride, myristylbenzyldimethylammonium chloride, palmitylbenzyldimethylammonium chloride, and stearylbenzyldimethylammonium chloride are preferred, myristylbenzyldimethylammonium chloride, tetramethylammonium bromide, tetraethylammonium bromide, hexyltrimethylammonium bromide, and phenyltrimethylammonium chloride are more preferred, and myristylbenzyldimethylammonium chloride is even more preferred.

(Amine)

As the amine in the present invention, a monoamine, a diamine, or a polyamide having a ratio of carbon atoms to nitrogen atom or atoms per molecule of the compound (number of carbon atoms/number of nitrogen atoms) of 3 or more and 45 or less can be used. Each amine will be described hereinbelow.

Specific examples of the monoamine usable in the present invention include, for example, a compound represented by the general formula (2):

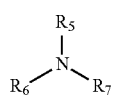

(2)

wherein each of $R_5$, $R_6$, and $R_7$, which may be identical or different, is a hydrogen atom, an alkyl group or a hydroxyalkyl group each having from 1 to 10 carbon atoms, an aryl group having from 6 to 20 carbon atoms, an aralkyl group having from 7 to 20 carbon atoms, or a heteroaromatic ring group.

Specific examples of the alkyl group and the hydroxyalkyl group in the general formula (2) include, of those exemplified as the alkyl group in the general formula (1), alkyl groups having from 1 to 10 carbon atoms, and groups in which these alkyl groups are substituted with a hydroxy group.

The aryl group in the general formula (2) has the number of carbon atoms of preferably from 6 to 20, more preferably from 6 to 14, and even more preferably from 6 to 10, and the same ones as the aryl group in the general formula (1) are exemplified.

The aralkyl group in the general formula (2) has the number of carbon atoms of preferably from 7 to 20, more preferably from 7 to 14, and even more preferably from 7 to 10, and the same ones as the aralkyl group in the general formula (1) are exemplified.

The heteroaromatic ring group in the general formula (2) includes a pyrrole group, an imidazole group, a pyrazole group, an indole group, a pyridine group, a benzimidazole group, a phenothiazine group, and the like.

Among them, each of $R_5$, $R_6$, and $R_7$, which may be identical or different, is preferably a hydrogen atom, an alkyl group or a hydroxyalkyl group each having from 1 to 10 carbon atoms, or a heteroaromatic ring group, and more preferably a hydrogen atom or an alkyl group having from 1 to 10 carbon atoms, from the viewpoint of exhibiting a thickening aiding effect and thermal stability.

The monoamine has the above ratio (number of carbon atoms/number of nitrogen atoms) of preferably 3 or more, more preferably 4 or more, and even more preferably 5 or more, from the viewpoint of a thickening aiding effect and thermal stability, and water solubility. In addition, the monoamine has the above ratio of preferably 16 or less, more preferably 12 or less, even more preferably 10 or less, and still even more preferably 8 or less, from the viewpoint of a thickening aiding effect and thermal stability, and water solubility.

The monoamine has the number of carbon atoms per molecule of the compound of preferably 3 or more, more preferably 4 or more, and even more preferably 5 or more, from the viewpoint of exhibiting a thickening aiding effect and thermal stability. The monoamine has the number of carbon atoms of preferably 16 or less, more preferably 12 or less, even more preferably 10 or less, and still even more preferably 8 or less, from the viewpoint of water solubility.

The monoamine has the number of nitrogen atoms per molecule of the compound of preferably 1 or more, from the viewpoint of exhibiting a thickening aiding effect and thermal stability. In addition, the monoamine has the number of nitrogen atoms of preferably 4 or less, more preferably 3 or less, and even more preferably 2 or less, from the viewpoint of exhibiting a thickening aiding effect and thermal stability.

The monoamine has a molecular weight of preferably 60 or more, more preferably 80 or more, and even more preferably 100 or more, from the viewpoint of exhibiting a thickening aiding effect and thermal stability. In addition, the monoamine has a molecular weight of preferably 650 or less, more preferably 300 or less, and even more preferably 150 or less, from the viewpoint of exhibiting a thickening aiding effect and thermal stability.

The monoamine usable in the present invention may be any of primary amines, secondary amines, and tertiary amines.

Specific examples of the compound represented by the general formula (2) include:
primary monoamines: propylamine, butylamine, pentylamine, hexylamine, octylamine, decylamine, dodecylamine, polyoxyethyleneamine (degree of polymerization: 1 to 6), polyoxypropyleneamine (degree of polymerization: 1 to 4), and polyoxyethylene/propyleneamine (degree of polymerization: 1 to 5);
secondary monoamines: diethylamine, dipropylamine, dibutylamine, dipentylamine, dihexylamine, dioctylamine, didecylamine, and diethanolamine; and
tertiary monoamines: trimethylamine, triethylamine, tripropylamine, tributylamine, tripentylamine, trihexylamine, trioctylamine, triethanolamine, dimethylaminoethanol, dimethylaminopropanol, dimethylaminobutanol, dimethylaminopentanol, dimethylaminohexanol, dimethylaminooctanol, dimethylaminodecanol, and N,N-dimethyl-4-aminopyridine.

These monoamines can be used alone or in combination of two or more kinds, and those produced in accordance with known methods and commercially available products can be used.

In particular, from the viewpoint of exhibiting a thickening aiding effect and thermal stability,
primary monoamines: pentylamine, hexylamine, and octylamine,
secondary monoamines: diethylamine, dipropylamine, and dibutylamine, and
tertiary monoamines: triethylamine, tripropylamine, dimethylaminohexanol, and N,N-dimethyl-4-aminopyridine, are preferred,
hexylamine, dipropylamine, triethylamine, dimethylaminohexanol, and N,N-dimethyl-4-aminopyridine are more preferred, and
dimethylaminohexanol is even more preferred.

Specific examples of the diamine usable in the present invention include, for example, a compound represented by the general formula (3):

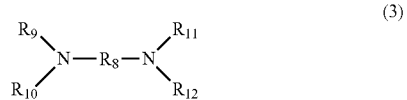

wherein $R_8$ is a (cyclo)alkylene group having from 3 to 18 carbon atoms or a polyoxyalkylene group having from 3 to 24 carbon atoms; and each of $R_9$, $R_{10}$, $R_{11}$, and $R_{12}$, which may be identical or different, is a hydrogen atom or a methyl group.

The (cyclo)alkylene group in the general formula (3) is an alkylene group or a cycloalkylene group each having preferably from 3 to 18 carbon atoms. Specific examples include a propylene group, a cyclopropylene group, a butylene group, a cyclobutylene group, a pentylene group, a cyclopentylene group, a hexylene group, a cyclohexylene group, a heptylene group, an octylene group, a nonylene group, a decylene group, an undecylene group, a dodecylene group, a tridecylene group, a tetradecylene group, a hexadecylene group, an octadecylene group, and groups in which an alkylene group in these (cyclo)alkylene groups is substituted with the same functional groups as in the above general formula (1).

The polyoxyalkylene group in the general formula (3) has the number of carbon atoms of preferably from 3 to 24, and more preferably from 5 to 14. Specific examples include, of those exemplified as the polyoxyalkylene group in the general formula (2), the polyoxyalkylene group having from 3 to 24 carbon atoms.

The diamine has the above ratio (number of carbon atoms/number of nitrogen atoms) of preferably 5 or more, and more preferably 6 or more, from the viewpoint of a thickening aiding effect and thermal stability, and water solubility. In addition the diamine has the above ratio of preferably 16 or less, more preferably 12 or less, even more preferably 10 or less, and still even more preferably 8 or less, from the viewpoint of a thickening aiding effect and thermal stability, and water solubility.

The diamine has the number of carbon atoms per molecule of the compound of preferably 3 or more, more preferably 5 or more, and even more preferably 8 or more, from the viewpoint of exhibiting a thickening aiding effect and thermal stability. In addition, the diamine has the number of carbon atoms of preferably 30 or less, more preferably 20 or less, and even more preferably 14 or less, from the viewpoint of water solubility.

The diamine has the number of nitrogen atoms per molecule of the compound of preferably 2 or more, from the viewpoint of exhibiting a thickening aiding effect and thermal stability. In addition, the diamine has the number of nitrogen atoms of preferably 5 or less, more preferably 4 or less, and even more preferably 3 or less, from the viewpoint of exhibiting a thickening aiding effect and thermal stability.

The diamine has a molecular weight of preferably 70 or more, and more preferably 100 or more, from the viewpoint of exhibiting a thickening aiding effect and thermal stability. In addition, the diamine has a molecular weight of preferably 1,000 or less, more preferably 600 or less, and even more preferably from 400 or less, from the viewpoint of exhibiting a thickening aiding effect and thermal stability.

The diamine usable in the present invention may be any of primary diamines, secondary diamines, and tertiary diamines, and from the viewpoint of availability, the primary diamines or the tertiary diamines are preferred.

Specific examples of the compound represented by the general formula (3) include:
primary diamines: 1,4-cyclohexanediamine, 1,6-hexanediamine, 1,7-heptanediamine, 1,8-octanediamine, 1,9-nonanediamine, 1,10-decanediamine, 1,11-undecanediamine, 1,12-dodecanediamine, 1,13-tridecanediamine, 1,14-tetradecanediamine, polyoxyethylenediamine (degree of polymerization: 1 to 15, 2 to 10, 3 to 8), polyoxypropylenediamine (degree of polymerization: 1 to 10, 2 to 7), and polyoxyethylene/propylenediamine (degree of polymerization: 1 to 12, 2 to 8, 3 to 7); and
tertiary diamines: N,N,N,N-tetramethyl-1,2-ethanediamine, N,N,N,N-tetramethyl-1,3-propanediamine, N,N,N,N-tetramethyl-1,4-butanediamine, N,N,N,N-tetramethyl-1,5-pentanediamine, N,N,N,N-tetramethyl-1,6-hexanediamine, N,N,N,N-tetramethyl-1,8-octanediamine, N,N,N,N-tetramethyl-1,10-decanediamine, and N,N,N,N-tetramethyl-1,12-dodecanediamine.

These diamines can be used alone or in combination of two or more kinds, and those produced in accordance with known methods and commercially available products can be used. For example, as trioxypropylenediamine, JEFFAMINE D-230 manufactured by Mitsui Chemical, or as hexoxypropylenediamine, JEFFAMINE D-400 manufactured by Mitsui Chemical can be used.

In particular, from the viewpoint of exhibiting a thickening aiding effect and thermal stability,
primary diamines: 1,4-cyclohexanediamine, 1,6-hexanediamine, 1,7-heptanediamine, 1,8-octanediamine, 1,9-nonanediamine, 1,10-decanediamine, 1,11-undecanediamine, 1,12-dodecanediamine, 1,13-tridecanediamine, 1,14-tetradecanediamine, and polyoxypropylenediamine (degree of polymerization: 1 to 10, 2 to 7); and
tertiary diamines: N,N,N,N-tetramethyl-1,5-pentanediamine, N,N,N,N-tetramethyl-1,6-hexanediamine, N,N,N,N-tetramethyl-1,8-octanediamine, N,N,N,N-tetramethyl-1,10-decanediamine, and N,N,N,N-tetramethyl-1,12-dodecanediamine,
are preferred,
cyclohexanediamine, tetramethylhexanediamine, trioxypropylenediamine, dodecanediamine, and hexoxypropylenediamine are more preferred, and trioxypropylenediamine and dodecanediamine are even more preferred.

Specific examples of the polyamine usable in the present invention include, for example, a triamine represented by the general formula (4):

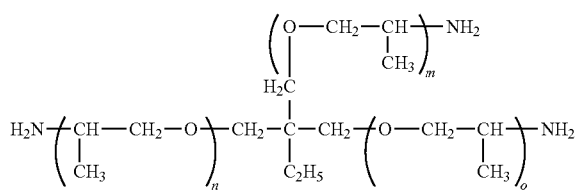

(4)

wherein each of m, n, and o is independently an average number of moles added of an oxypropylene group, wherein m+n+o is a number satisfying 1 or more and 12 or less.

Each of m, n, and o in the general formula (4) is independently an average number of moles added of an oxypropylene group, wherein m+n+o is a number satisfying preferably 1 or more, more preferably 3 or more, and even more preferably 4 or more, and preferably 12 or less, more preferably 8 or less, and even more preferably 6 or less.

The compound of the general formula (4) has the above ratio (number of carbon atoms/number of nitrogen atoms) of preferably 5 or more, and more preferably 6 or more, from the viewpoint of a thickening aiding effect and thermal stability, and water solubility. In addition, the compound has the above ratio of preferably 16 or less, more preferably 12 or less, and even more preferably 9 or less, from the viewpoint of a thickening aiding effect and thermal stability, and water solubility.

The compound of the general formula (4) has the number of carbon atoms per molecule of the compound of preferably 9 or more, more preferably 15 or more, and even more preferably 18 or more, from the viewpoint of exhibiting a thickening aiding effect and thermal stability. In addition, the compound has the number of carbon atoms of preferably 42 or less, more preferably 30 or less, and even more preferably 24 or less, from the viewpoint of exhibiting a thickening aiding effect and thermal stability.

The compound of the general formula (4) has a molecular weight of preferably 180 or more, more preferably 300 or more, and even more preferably 350 or more, from the viewpoint of exhibiting a thickening aiding effect and thermal stability. In addition, the compound has a molecular weight of preferably 850 or less, more preferably 600 or less, and even more preferably 500 or less, from the viewpoint of exhibiting a thickening aiding effect and thermal stability.

Specific examples of the compound represented by the general formula (4) include polyoxypropylenetriamine (degree of polymerization: 2 to 14, degree of polymerization: 3 to 10, degree of polymerization: 3 to 8). These compounds can be used alone or in combination of two or more kinds, and those produced in accordance with known methods and commercially available products can be used. For example, as pentoxypropylenetriamine, JEFFAMINE T-403 manufactured by Mitsui Chemical can be used.

In addition, the polyamine in the present invention includes a compound represented by the general formula (5):

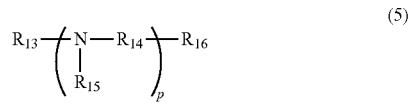

(5)

wherein $R_{13}$ is a hydrogen atom, a hydroxy group, or an alkyl group or a hydroxyalkyl group each having from 1 to 10 carbon atoms; $R_{14}$ is an alkylene group having from 1 to 8 carbon atoms; $R_{15}$ is a hydrogen atom, a hydroxy group, or an alkyl group or a hydroxyalkyl group each having from 1 to 6 carbon atoms; $R_{16}$ is a hydrogen atom or a hydroxy group; and p is from 3 to 6.

$R_{13}$ in the general formula (5) is a hydrogen atom, a hydroxy group, or an alkyl group or a hydroxyalkyl group each having from 1 to 10 carbon atoms. The alkyl group or the hydroxyalkyl each group having from 1 to 10 carbon atoms includes the same ones as the alkyl group or the hydroxyalkyl group in the general formula (2), and those having 4 to 8 carbon atoms are preferred. Among them, it is preferable that $R_{13}$ is a hydroxyalkyl group having from 1 to 10 carbon atoms.

$R_{14}$ in the general formula (5) is an alkylene group having from 1 to 8 carbon atoms. Specific examples include a methylene group, an ethylene group, a propylene group, a butylene group, a pentylene group, a hexylene group, a heptylene group, an octylene group, and groups in which these alkylene groups are substituted with a substituent in the general formula (1). In particular, those having 4 to 6 carbon atoms are preferred.

$R_{15}$ in the general formula (5) is a hydrogen atom, a hydroxy group, or an alkyl group or a hydroxyalkyl group each having from 1 to 6 carbon atoms. The alkyl group or the hydroxyalkyl group each having from 1 to 6 carbon atoms includes, of those alkyl groups or hydroxyalkyl groups exemplified in the general formula (2), those having from 1 to 6 carbon atoms, and in particular, those having from 1 to 3 carbon atoms are preferred.

$R_{16}$ in the general formula (5) is a hydrogen atom or a hydroxy group.

p in the general formula (5) is preferably from 3 to 6, more preferably from 3 to 5, and even more preferably from 3 to 4.

The compound of the general formula (5) has the above ratio (number of carbon atoms/number of nitrogen atoms) of preferably 5 or more, more preferably 6 or more, and even more preferably 8 or more, from the viewpoint of a thickening aiding effect and thermal stability, and water solubility. In addition, the compound has the above ratio of preferably 16 or less, more preferably 12 or less, and even more preferably 9 or less, from the viewpoint of a thickening aiding effect and thermal stability, and water solubility.

The compound of the general formula (5) has the number of carbon atoms per molecule of the compound of preferably 10 or more, more preferably 15 or more, even more preferably 20 or more, and still even more preferably 25 or more, from the viewpoint of exhibiting a thickening aiding effect and thermal stability. In addition, the compound has the number of carbon atoms of preferably 50 or less, more preferably 45 or less, even more preferably 42 or less, and still even more preferably 30 or less, from the viewpoint of exhibiting a thickening aiding effect and thermal stability.

The compound of the general formula (5) has the number of nitrogen atoms per molecule of the compound of 3 or more, and from the viewpoint of availability, and the compound has the number of nitrogen atoms of preferably 6 or less, more preferably 5 or less, and even more preferably 4 or less.

The compound of the general formula (5) has a molecular weight of preferably 70 or more, more preferably 100 or more, and even more preferably 130 or more, from the viewpoint of exhibiting a thickening aiding effect and thermal stability. In addition, the compound has a molecular weight of preferably 2,000 or less, more preferably 1,500 or less, and even more preferably 1,000 or less, from the viewpoint of availability.

Specific examples of the compound represented by the general formula (5) include mono-tertiary amine glycols, di-tertiary amine glycols, tri-tertiary amine glycols, tetra-tertiary amine glycols, penta-tertiary amine glycols, and hexa-tertiary amine glycols. These compounds can be used alone or in combination of two or more kinds, and those produced in accordance with known methods and commercially available products can be used. For example, as a tri-tertiary amine glycol, Kaolizer P-200 manufactured by Kao Corporation can be used.

(Amide)

The amide usable in the present invention includes, for example, a compound represented by the formula (6):

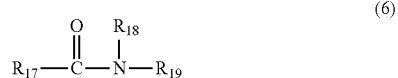

(6)

wherein $R_{17}$ is an alkyl group having from 6 to 18 carbon atoms; and each of $R_{18}$ and $R_{19}$, which may be identical or different, is a hydrogen atom or an alkyl group or a hydroxyalkyl group each having from 1 to 8 carbon atoms,
the compound having a ratio of carbon atoms to nitrogen atom or atoms per molecule of the compound (number of carbon atoms/number of nitrogen atoms) of 3 or more and 45 or less.

The alkyl group having from 6 to 18 carbon atoms in the general formula (6) includes, out of those exemplified in the alkyl group in the general formula (1), those alkyl groups having from 6 to 18 carbon atoms, and in particular, those alkyl groups having from 8 to 16 carbon atoms are preferred, and those alkyl groups having from 10 to 14 carbon atoms are more preferred.

The alkyl group or the hydroxyalkyl group each having from 1 to 8 carbon atoms in the general formula (6) includes, out of those exemplified in the alkyl group or the hydroxyalkyl group in the general formula (2), those groups having from 1 to 8 carbon atoms, and in particular, those groups having from 1 to 5 carbon atoms are preferred.

The compound of the general formula (6) has the above ratio (number of carbon atoms/number of nitrogen atoms) of preferably 4 or more, more preferably 6 or more, and even more preferably 10 or more, from the viewpoint of a thickening aiding effect and thermal stability. In addition, the compound has the above ratio of preferably 40 or less, more preferably 35 or less, even more preferably 30 or less, and still even more preferably 25 or less, from the viewpoint of a thickening aiding effect and thermal stability.

The compound of the general formula (6) has the number of carbon atoms per molecule of the compound of preferably 3 or more, more preferably 10 or more, and even more preferably 14 or more, from the viewpoint of exhibiting a thickening aiding effect and thermal stability. In addition, the compound has the number of carbon atoms of preferably 25 or less, more preferably 20 or less, and even more preferably 18 or less, from the viewpoint of exhibiting a thickening aiding effect and thermal stability.

The compound of the general formula (6) has a molecular weight of preferably 70 or more, more preferably 100 or more, and even more preferably 150 or more, from the viewpoint of exhibiting a thickening aiding effect and thermal stability. In addition, the compound has a molecular weight of preferably 500 or less, more preferably 350 or less, and even more preferably 300 or less, from the viewpoint of exhibiting a thickening aiding effect and thermal stability.

Specific examples of the compound represented by the general formula (6) include
octylmonoethanolamide, decylmonoethanolamide, laurylmonoethanolamide, myristylmonoethanolamide, palmitylmonoethanolamide, stearylmonoethanolamide, oleylmonoethanolamide,
octyldiethanolamide, decyldiethanolamide, lauryldiethanolamide, myristyldiethanolamide, palmityldiethanolamide, stearyldiethanolamide, oleyldiethanolamide, octylmethylethanolamide, decylmethylethanolamide, laurylmethylethanolamide, myristylmethylethanolamide, palmitylmethylethanolamide, stearylmethylethanolamide, and oleylmethylethanolamide.
These compounds can be used alone or in combination of two or more kinds, and those produced in accordance with known methods and commercially available products can be used.

In particular, from the viewpoint of exhibiting a thickening aiding effect and thermal stability,
myristylmonoethanolamide, palmitylmonoethanolamide, stearylmonoethanolamide, oleylmonoethanolamide,
decyldiethanolamide, lauryldiethanolamide, and myristyldiethanolamide are preferred, and lauryldiethanolamide is more preferred.

In the present invention, as the compound having the above ratio, it is preferable to use one or more compounds selected from the group consisting of these quaternary ammonium salts, amines, and amides, and the content of the quaternary ammonium salt, the amine, and the amide mentioned above in the component (B) is preferably 50% by mass or more, more preferably 80% by mass or more, even more preferably 90% by mass or more, and even more preferably substantially 100% by mass, from the viewpoint of exhibiting a thickening aiding effect and thermal stability. Here, in the present specification, the content of the quaternary ammonium salt, the amine, and the amide mentioned above constituting the above additive means a total content when plural compounds are contained.

The water-based composition of the present invention can contain, besides the inclusion of the above components (A) and (B), a clay mineral, a disintegration inhibitor, a specific gravity conditioner, a water-soluble polymer, an ultraviolet protective agent, a moisturizing agent, a defoaming agent, a dispersant, an alcohol, a surfactant, an anti-corrosive agent, an antioxidant, a chelating agent, a pH adjustment agent or the like, within the range that would not impair the effects of the present invention. The contents of those additives are not particularly limited.

The content of the above component (A) in the water-based composition of the present invention is 0.2% by mass or more and 10% by mass or less, and the content is preferably 0.3% by mass or more, and more preferably 0.4% by mass or more, from the viewpoint of thickening effects. In addition, the content is preferably 5% by mass or less, more preferably 3% by mass or less, even more preferably 1% by mass or less, and still even more preferably 0.7% by mass or less, from the viewpoint of handling property and costs.

The content of the above component (B) in the water-based composition of the present invention is preferably 0.02% by mass or more, more preferably 0.05% by mass or more, even more preferably 0.07% by mass or more, and still even more preferably 0.09% by mass or more, from the viewpoint of exhibiting a thickening aiding effect and thermal stability. In addition, the content is preferably 1% by mass or less, more preferably 0.5% by mass or less, even more preferably 0.3% by mass or less, even more preferably 0.2% by mass or less, and still even more preferably 0.15% by mass or less, from the viewpoint of a thickening aiding effect, thermal stability, and costs.

In addition, the content of the above component (B), based on 100 parts by mass of the component (A), is 3 parts by mass or more and 150 parts by mass or less, and the content is preferably 5 parts by mass or more, more preferably 10 parts by mass or more, and even more preferably 15 parts by mass or more, from the viewpoint of exhibiting a thickening aiding effect and thermal stability. In addition, the content is preferably 100 parts by mass or less, more preferably 50 parts by mass or less, even more preferably 40 parts by mass or less, and still even more preferably 30 parts by mass or less, from the viewpoint of a thickening aiding effect, thermal stability, and costs.

The water-based composition of the present invention can be prepared by a known method, so long as the water-based composition contains the above components (A) and (B). For example, a water-based composition is obtained by dispersing the above components in an aqueous medium. The aqueous medium refers to a liquid medium containing at least 10% by mass of water. The content of the aqueous medium in the water-based composition is not particularly limited, and the content is preferably 30% by mass or more, more preferably 40% by mass or more, even more preferably 50% by mass or more, even more preferably 70% by mass or more, even more preferably 80% by mass or more, and even more preferably 90% by mass or more, from the viewpoint of exhibiting thickening property. Although an upper limit thereof is not particularly limited, the content is preferably 99.7% by mass or less.

The water-based composition of the present invention obtained shows a viscosity at 80° C. and a rotational speed of 30 rpm of 80 mPa·s or more. The water-based composition has a viscosity of preferably 90 mPa·s or more, more preferably 100 mPa·s or more, and even more preferably 120 mPa·s or more, from the viewpoint of obtaining a viscous liquid. In addition, the water-based composition has a viscosity of preferably 100,000 mPa·s or less, more preferably 50,000 mPa·s or less, even more preferably 30,000 mPa·s or less, and still even more preferably 10,000 mPa·s or less, from the viewpoint of handling property. Here, the viscosity as used herein refers to a value measured with a B-type viscometer.

In addition, the water-based composition of the present invention shows a high viscosity even at a high-temperature, in other words, the fluctuations in viscosities in the temperature region from an ambient temperature to a high temperature are small. Therefore, the water-based composition has a ratio of a viscosity at 80° C. to a viscosity at 25° C. (80° C./25° C.) at a rotational speed of 30 rpm is preferably from 0.6 to 3.5, more preferably from 0.7 to 2.0, and even more preferably from 0.8 to 1.5.

Furthermore, the water-based composition of the present invention has also excellent thixotropy. For example, the water-based composition has a ratio of a viscosity at a rotational speed of 3 rpm to a viscosity at a rotational speed of 30 rpm (3 rpm/30 rpm) at a temperature of 25° C. of preferably 2 or more, more preferably 2.5 or more, and even more preferably 3 or more. In addition, the upper limit of the ratio is not particularly limited, and the compound has the above ratio of 10 or so.

Since the water-based composition of the present invention has favorable processability, and excellent thickening property and heat resistance, the water-based composition can be suitably used in cosmetics such as creams, milky lotions, and lipsticks, household articles such as fragrance, shampoos, and hairdyes, industrial manufactured articles such as blowing agents, paints and concrete.

Since the water-based composition of the present invention has favorably processability and excellent heat resistance, the water-based composition can be suitably used in piling construction and underground extraction of petroleum or the like. Specifically, it is preferable to use the water-based composition as any one of fluids selected from the group consisting of drilling fluids, spacer fluids, injection fluids for well stimulations, and displacement fluids for enhanced oil recovery.

Since the present invention also exhibits a favorable viscosity even at a high temperature, for example, methods of the following embodiment 1 and embodiment 2 are provided as embodiments in which a water-based composition of the present invention is used.

Embodiment 1

A method for treating an underground layer characterized in that the method includes treating an underground layer with a water-based composition of the present invention.

Embodiment 2

A method for recovering earth and sand or rocks generated by drilling, including feeding a water-based composition of the present invention to a tip end of an underground drilling hole, and recovering earth and sand or rocks generated by drilling aboveground.

In Embodiment 1, a natural gas or a crude oil in an underground layer can be extracted by using a water-based composition of the present invention as, for example, any one of fluids selected from the group consisting of drilling fluids, spacer fluids, injection fluids for well stimulations, and displacement fluids for enhanced oil recovery. Here, since a water-based composition of the present invention has excellent heat resistance, while the water-based composition can be applied in the same manner as conventional drilling fluids, spacer fluids, injection fluids for well stimulations, and displacement fluids for enhanced oil recovery, an effect of improving workability is exhibited.

In Embodiment 2, a water-based composition of the present invention is fed to a tip end of an underground drilling hole, to disperse earth and sand or rocks generated by drilling in the water-based composition of the present invention, thereby exhibiting an effect of being easily recovered aboveground due to its thickening effect. For example, the water-based composition is suitably used in well drilling in the oil fields.

With respect to the above-mentioned embodiments, the present invention further discloses the following water-based compositions and uses thereof.

<1> A water-based composition containing:
(A) fine cellulose fibers having a number-average fiber diameter of 0.5 nm or more and 200 nm or less, and having a carboxy group content of 0.1 mmol/g or more, wherein the carboxy group forms a salt with an alkali metal; and
(B) an additive containing one or more compounds having carbon atoms and nitrogen atom or atoms, wherein a ratio thereof per molecule of the compound (number of carbon atoms/number of nitrogen atoms) is 3 or more and 45 or less, wherein the content of the above component (A) is 0.2% by mass or more and 10% by mass or less, and wherein the content of the above component (B) is 3 parts by mass or more and 150 parts by mass or less, based on 100 parts by mass of the component (A), and wherein the water-based composition has a viscosity at 80° C. at a rotational speed of 30 rpm of 80 mPa·s or more.

<2> The water-based composition according to the above <1>, wherein the fine cellulose fibers have a number-average fiber diameter of preferably 0.8 nm or more, and more preferably 1.0 nm or more, and preferably 100 nm or less, more preferably 50 nm or less, even more preferably 20 nm or less, even more preferably 10 nm or less, and still even more preferably 5 nm or less.

<3> The water-based composition according to the above <1> or <2>, wherein the fine cellulose fibers have a carboxy group content of preferably 0.4 mmol/g or more, more preferably 0.6 mmol/g or more, and even more preferably 0.8 mmol/g or more, and preferably 3.0 mmol/g or less, more preferably 2.7 mmol/g or less, even more preferably 2.5 mmol/g or less, and still even more preferably 2.0 mmol/g or less.

<4> The water-based composition according to any one of the above <1> to <3>, wherein the alkali metal in the fine cellulose fibers in the form of a salt is preferably Li, Na, K, or Rb, more preferably Na or K, and even more preferably Na.

<5> The water-based composition according to any one of the above <1> to <4>, wherein the fine cellulose fibers have an average aspect ratio (fiber length/fiber diameter) of preferably 10 or more, more preferably 20 or more, even more preferably 50 or more, still even more preferably 100 or more, and still even more preferably 200 or more, and preferably 1,000 or less, more preferably 500 or less, even more preferably 400 or less, and still even more preferably 350 or less.

<6> The water-based composition according to any one of the above <1> to <5>, wherein the fine cellulose fibers are obtainable by a method including oxidizing natural cellulose fibers in the presence of an N-oxyl compound, to provide an alkali metal salt form of carboxy group-containing cellulose fibers (oxidization treatment step); and subjecting the resulting fibers to a finely pulverizing treatment (finely pulverizing step).

<7> The water-based composition according to the above <6>, wherein as the N-oxyl compound, one or more heterocyclic N-oxyl compounds selected from piperidinoxyl compounds, pyrrolidinoxyl compounds, imidazolinoxyl compounds, and azaadamantane compounds having an alkyl group having 1 or 2 carbon atoms are preferred, the piperidinoxyl compounds having an alkyl group having 1 or 2 carbon atoms are more preferred, a 2,2,6,6-tetramethylpiperidin-1-oxyl (TEMPO), a 4-hydroxy-2,2,6,6-tetramethylpiperidin-1-oxyl, and a 4-methoxy-2,2,6,6-tetramethylpiperidin-1-oxyl are even more preferred, and a 2,2,6,6-tetramethylpiperidin-1-oxyl (TEMPO) is even more preferred.

<8> The water-based composition according to any one of the above <1> to <7>, wherein the component (B) contains one or more compounds selected from the group consisting of quaternary ammonium salts, amines, and amides, each having carbon atoms and nitrogen atom or atoms, wherein a ratio thereof per molecule of the compound (number of carbon atoms/number of nitrogen atoms) is 3 or more and 45 or less.

<9> The water-based composition according to the above <8>, wherein the quaternary ammonium salt has a ratio of carbon atoms to nitrogen atom or atoms per molecule of the compound (number of carbon atoms/number of nitrogen atoms) of preferably 4 or more, more preferably 6 or more, and even more preferably 20 or more, and preferably 40 or less, more preferably 35 or less, even more preferably 30 or less, and still even more preferably 25 or less, and has the number of carbon atoms per molecule of the compound of preferably 4 or more, more preferably 6 or more, even more preferably 12 or more, and even more preferably 18 or more, and preferably 45 or less, more preferably 35 or less, even more preferably 30 or less, and even more preferably 25 or less, and has the number of nitrogen atom or atoms per molecule of the compound of preferably 1 or more and 2 or less, and more preferably 1.

<10> The water-based composition according to the above <8> or <9>, wherein the quaternary ammonium salt has a molecular weight of preferably 70 or more, more preferably 100 or more, even more preferably 200 or more, even more preferably 300 or more, and still even more preferably 350 or more, and preferably 500 or less, and more preferably 400 or less.

<11> The water-based composition according to any one of the above <8> to <10>, wherein the quaternary ammonium salt is preferably a compound represented by the general formula (1):

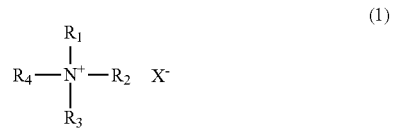

wherein each of $R_1$, $R_2$, $R_3$, and $R_4$, which may be identical or different, is an alkyl group having from 1 to 20 carbon atoms, an aryl group having from 6 to 20 carbon atoms, or an aralkyl group having from 7 to 20 carbon atoms; and X is F, Br, Cl, or I.

<12> The water-based composition according to the above <11>, wherein the compound represented by the general formula (1) includes
tetramethylammonium halides, tetraethylammonium halides, tetrapropylammonium halides, tetrabutylammonium halides, tetrapentylammonium halides, tetrahexylammonium halides, tetraphenylammonium halides, tetrabenzylammonium halides,
ethyltrimethylammonium halides, propyltrimethylammonium halides, butyltrimethylammonium halides, pentyltrimethylammonium halides, hexyltrimethylammonium halides, octyltrimethylammonium halides, decyltrimethylammonium halides, dodecyltrimethylammonium halides, tetradecyltrimethylammonium halides, hexadecyltrimethylammonium halides, octadecyltrimethylammonium halides, phenyltrimethylammonium halides, benzyltrimethylammonium halides,
pentyltripropylammonium chloride, hexyltripropylammonium chloride, octyltripropylammonium chloride, decyltripropylammonium chloride, phenyltripropylammonium chloride, benzyltripropylammonium chloride,
dioctyldimethylammonium halides, didecyldimethylammonium halides, didodecyldimethylammonium halides, dimyristyldimethylammonium halides,
butylbenzyldimethylammonium chloride, pentylbenzyldimethylammonium chloride, hexylbenzyldimethylammonium chloride, octylbenzyldimethylammonium chloride, decylbenzyldimethylammonium chloride, dodecylbenzyldimethylammonium chloride, myristylbenzyldimethylammonium chloride, palmitylbenzyldimethylammonium chloride, and stearylbenzyldimethylammonium chloride, and
in particular,
tetramethylammonium halides, tetraethylammonium halides, tetrapropylammonium halides, tetrabutylammonium halides,
pentyltrimethylammonium halides, hexyltrimethylammonium halides, octyltrimethylammonium halides, decyltrimethylammonium halides, dodecyltrimethylammonium halides, tetradecyltrimethylammonium halides, hexadecyltrimethylammonium halides, octadecyltrimethylammonium halides, phenyltrimethylammonium halides, benzyltrimethylammonium halides,
phenyltripropylammonium chloride,
dioctyldimethylammonium halides, didecyldimethylammonium halides, didodecyldimethylammonium halides, dimyristyldimethylammonium halides,
octylbenzyldimethylammonium chloride, decylbenzyldimethylammonium chloride, dodecylbenzyldimethylammonium chloride, myristylbenzyldimethylammonium chloride, palmitylbenzyldimethylammonium chloride, and stearylbenzyldimethylammonium chloride are preferred,
myristylbenzyldimethylammonium chloride, tetramethylammonium bromide, tetraethylammonium bromide, hexyltrimethylammonium bromide, and phenyltripropylammonium chloride are more preferred, and
myristylbenzyldimethylammonium chloride is even more preferred.

<13> The water-based composition according to the above <8>, wherein as the amine, a monoamine, a diamine, or a polyamide having a ratio of carbon atoms to nitrogen atom or atoms per molecule of the compound (number of carbon atoms/number of nitrogen atoms) of 3 or more and 45 or less can be used.

<14> The water-based composition according to the above <13>, wherein the monoamine is preferably a compound represented by the general formula (2):

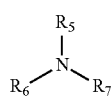

(2)

wherein each of $R_5$, $R_6$, and $R_7$, which may be identical or different, is a hydrogen atom, an alkyl group or a hydroxyalkyl group each having from 1 to 10 carbon atoms, an aryl group having from 6 to 20 carbon atoms, an aralkyl group having from 7 to 20 carbon atoms, or a heteroaromatic ring group.

<15> The water-based composition according to the above <13> or <14>, wherein the monoamine has a ratio of carbon atoms to nitrogen atom or atoms per molecule of the compound (number of carbon atoms/number of nitrogen atoms) of preferably 3 or more, more preferably 4 or more, and even more preferably 5 or more, and preferably 16 or less, more preferably 12 or less, even more preferably 10 or less, and still even more preferably 8 or less, and has the number of carbon atoms per molecule of the compound of preferably 3 or more, more preferably 4 or more, and even more preferably 5 or more, and preferably 16 or less, more preferably 12 or less, even more preferably 10 or less, and still even more preferably 8 or less, and has the number of nitrogen atoms per molecule of the compound of preferably 1 or more, and preferably 4 or less, more preferably 3 or less, and even more preferably 2 or less.

<16> The water-based composition according to any one of the above <13> to <15>, wherein the monoamine has a molecular weight of preferably 60 or more, more preferably 80 or more, and even more preferably 100 or more, and preferably 650 or less, more preferably 300 or less, and even more preferably 150 or less.

<17> The water-based composition according to any one of the above <14> to <16>, wherein the compound represented by the general formula (2) includes:
primary monoamines: propylamine, butylamine, pentylamine, hexylamine, octylamine, decylamine, dodecylamine, polyoxyethyleneamine (degree of polymerization: 1 to 6), polyoxypropyleneamine (degree of polymerization: 1 to 4), and polyoxyethylene/propyleneamine (degree of polymerization: 1 to 5);
secondary monoamines: diethylamine, dipropylamine, dibutylamine, dipentylamine, dihexylamine, dioctylamine, didecylamine, and diethanolamine; and
tertiary monoamines: trimethylamine, triethylamine, tripropylamine, tributylamine, tripentylamine, trihexylamine, trioctylamine, triethanolamine, dimethylaminoethanol, dimethylaminopropanol, dimethylaminobutanol, dimethylaminopentanol, dimethylaminohexanol, dimethylaminooctanol, dimethylaminodecanol, and N,N-dimethyl-4-aminopyridine;
in particular,
primary monoamines: pentylamine, hexylamine, and octylamine,
secondary monoamines: diethylamine, dipropylamine, and dibutylamine, and
tertiary monoamines: triethylamine, tripropylamine, dimethylaminohexanol, and N,N-dimethyl-4-aminopyridine, are preferred,
hexylamine, dipropylamine, triethylamine, dimethylaminohexanol, and
N,N-dimethyl-4-aminopyridine are more preferred, and dimethylaminohexanol is even more preferred.

<18> The water-based composition according to the above <13>, wherein the diamine is preferably a compound represented by the general formula (3):

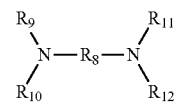

(3)

wherein $R_8$ is a (cyclo)alkylene group having from 3 to 18 carbon atoms or a polyoxyalkylene group having from 3 to 24 carbon atoms; and each of $R_9$, $R_{10}$, $R_{11}$, and $R_{12}$, which may be identical or different, is a hydrogen atom or a methyl group.

<19> The water-based composition according to the above <13> or <18>, wherein the diamine has a ratio of carbon atoms to nitrogen atom or atoms per molecule of the compound (number of carbon atoms/number of nitrogen atoms) of preferably 5 or more, and more preferably 6 or more, and preferably 16 or less, more preferably 12 or less, even more preferably 10 or less, and still even more preferably 8 or less, and has the number of carbon atoms per molecule of the compound of preferably 3 or more, more preferably 5 or more, and even more preferably 8 or more, and preferably 30 or less, more preferably 20 or less, and even more preferably 14 or less, and has the number of nitrogen atoms per molecule of the compound of preferably 2 or more, and preferably 5 or less, more preferably 4 or less, and even more preferably 3 or less.

<20> The water-based composition according to any one of the above <13>, <18>, and <19>, wherein the diamine has a molecular weight of preferably 70 or more, and more preferably 100 or more, and preferably 1,000 or less, more preferably 600 or less, and even more preferably from 400 or less.

<21> The water-based composition according to any one of the above <18> to <20>, wherein the compound represented by the general formula (3) includes:
primary diamines: 1,4-cyclohexanediamine, 1,6-hexanediamine, 1,7-heptanediamine, 1,8-octanediamine, 1,9-nonanediamine, 1,10-decanediamine, 1,11-undecanediamine, 1,12-dodecanediamine, 1,13-tridecanediamine, 1,14-tetradecanediamine, polyoxyethylenediamine (degree of polymerization: 1 to 15, 2 to 10, 3 to 8), polyoxypropylenediamine (degree of polymerization: 1 to 10, 2 to 7), and polyoxyethylene/propylenediamine (degree of polymerization: 1 to 12, 2 to 8, 3 to 7); and
tertiary diamines: N,N,N,N-tetramethyl-1,2-ethanediamine, N,N,N,N-tetramethyl-1,3-propanediamine, N,N,N,N-tetramethyl-1,4-butanediamine, N,N,N,N-tetramethyl-1,5-pentanediamine, N,N,N,N-tetramethyl-1,6-hexanediamine, N,N,N,N-tetramethyl-1,8-octanediamine, N,N,N,N-tetramethyl-1,10-decanediamine, and N,N,N,N-tetramethyl-1,12-dodecanediamine;
in particular,
primary diamines: 1,4-cyclohexanediamine, 1,6-hexanediamine, 1,7-heptanediamine, 1,8-octanediamine, 1,9-nonanediamine, 1,10-decanediamine, 1,11-undecanediamine, 1,12-dodecanediamine, 1,13-tridecanediamine, 1,14-tetradecanediamine, and polyoxypropylenediamine (degree of polymerization: 1 to 10, 2 to 7); and
tertiary diamines: N,N,N,N-tetramethyl-1,5-pentanediamine, N,N,N,N-tetramethyl-1,6-hexanediamine, N,N,N,N-tetramethyl-1,8-octanediamine, N,N,N,N-tetramethyl-1,10-decanediamine, and N,N,N,N-tetramethyl-1,12-dodecanediamine,
are preferred,
cyclohexanediamine, tetramethylhexanediamine, trioxypropylenediamine, dodecanediamine, and hexoxypropylenediamine are more preferred, and trioxypropylenediamine and dodecanediamine are even more preferred.

<22> The water-based composition according to the above <13>, wherein the polyamine is preferably a triamine represented by the general formula (4):

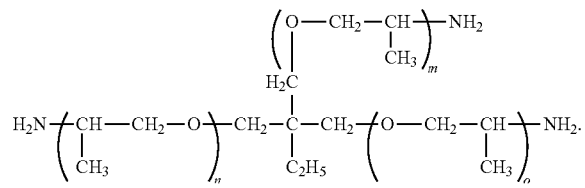

(4)

wherein each of m, n, and o is independently an average number of moles added of an oxypropylene group, wherein m+n+o is a number satisfying 1 or more and 12 or less.

<23> The water-based composition according to the above <22>, wherein the compound of the general formula (4) has a ratio of carbon atoms to nitrogen atom or atoms per molecule of the compound (number of carbon atoms/number of nitrogen atoms) of preferably 5 or more, and more preferably 6 or more, and preferably 16 or less, more preferably 12 or less, and even more preferably 9 or less, and has the number of carbon atoms per molecule of the compound of preferably 9 or more, more preferably 15 or more, and even more preferably 18 or more, and preferably 42 or less, more preferably 30 or less, and even more preferably 24 or less.

<24> The water-based composition according to the above <22> or <23>, wherein the compound of the general formula (4) has a molecular weight of preferably 180 or more, more preferably 300 or more, and even more preferably 350 or more, and preferably 850 or less, more preferably 600 or less, and even more preferably 500 or less.

<25> The water-based composition according to any one of the above <22> to <24>, wherein as the compound represented by the general formula (4), polyoxypropylenetriamine (degree of polymerization: 2 to 14, degree of polymerization: 3 to 10, degree of polymerization: 3 to 8) can be used.

<26> The water-based composition according to the above <13>, wherein the polyamine is preferably a compound represented by the general formula (5):

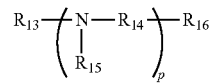

(5)

wherein $R_{13}$ is a hydrogen atom, a hydroxy group, or an alkyl group or a hydroxyalkyl group each having from 1 to 10 carbon atoms; $R_{14}$ is an alkylene group having from 1 to 8 carbon atoms; $R_{15}$ is a hydrogen atom, a hydroxy group, or an alkyl group or a hydroxyalkyl group each having from 1 to 6 carbon atoms; $R_{16}$ is a hydrogen atom or a hydroxy group; and p is from 3 to 6.

<27> The water-based composition according to the above <26>, wherein the compound of the general formula (5) has a ratio of carbon atoms to nitrogen atom or atoms per molecule of the compound (number of carbon atoms/number of nitrogen atoms) of preferably 5 or more, more preferably 6 or more, and even more preferably 8 or more, and preferably 16 or less, more preferably 12 or less, and even more preferably 9 or less, and has the number of carbon atoms per molecule of the compound of preferably 10 or more, more preferably 15 or more, even more preferably 20 or more, and still even more preferably 25 or more, and preferably 50 or less, more preferably 45 or less, even more preferably 42 or less, and still even more preferably 30 or less, and has the number of nitrogen atoms per molecule of the compound of 3 or more, and preferably 6 or less, more preferably 5 or less, and even more preferably 4 or less.

<28> The water-based composition according to the above <26> or <27>, wherein the compound of the general formula (5) has a molecular weight of preferably 70 or more, more preferably 100 or more, and even more preferably 130 or more, and preferably 2,000 or less, more preferably 1,500 or less, and even more preferably 1,000 or less.

<29> The water-based composition according to any one of the above <26> to <28>, wherein as the compound represented by the general formula (5), a mono-tertiary amine glycol, a di-tertiary amine glycol, a tri-tertiary amine glycol, a tetra-tertiary amine glycol, a penta-tertiary amine glycol, or a hexa-tertiary amine glycol can be used, alone or in combination of two or more kinds.

<30> The water-based composition according to the above <8>, wherein the amide is preferably a compound represented by the formula (6):

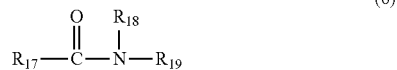

(6)

wherein $R_{17}$ is an alkyl group having from 6 to 18 carbon atoms; and each of $R_{18}$ and $R_{19}$, which may be identical or different, is a hydrogen atom or an alkyl group or a hydroxyalkyl group each having from 1 to 8 carbon atoms.

<31> The water-based composition according to the above <30>, wherein the compound of the general formula (6) has a ratio of carbon atoms to nitrogen atom or atoms per molecule of the compound (number of carbon atoms/number of nitrogen atoms) of preferably 4 or more, more preferably 6 or more, and even more preferably 10 or more, and preferably 40 or less, more preferably 35 or less, even more preferably 30 or less, and still even more preferably 25 or less, and has the number of carbon atoms per molecule of the compound of preferably 3 or more, more preferably 10 or more, and even more preferably 14 or more, and preferably 25 or less, more preferably 20 or less, and even more preferably 18 or less.

<32> The water-based composition according to the above <30> or <31>, wherein the compound of the general formula (6) has a molecular weight of preferably 70 or more, more preferably 100 or more, and even more preferably 150 or more, and preferably 500 or less, more preferably 350 or less, and even more preferably 300 or less.

<33> The water-based composition according to any one of the above <30> to <32>, wherein the compound represented by the general formula (6) includes
octylmonoethanolamide, decylmonoethanolamide, laurylmonoethanolamide, myristylmonoethanolamide, palmitylmonoethanolamide, stearylmonoethanolamide, oleylmonoethanolamide,
octyldiethanolamide, decyldiethanolamide, lauryldiethanolamide, myristyldiethanolamide, palmityldiethanolamide, stearyldiethanolamide, oleyldiethanolamide, octylmethylethanolamide, decylmethylethanolamide, laurylmethylethanolamide, myristylmethylethanolamide, palmitylmethylethanolamide, stearylmethylethanolamide, and oleylmethylethanolamide;
in particular,
myristylmonoethanolamide, palmitylmonoethanolamide, stearylmonoethanolamide, oleylmonoethanolamide,
decyldiethanolamide, lauryldiethanolamide, and myristyldiethanolamide are preferred, and
lauryldiethanolamide is more preferred.

<34> The water-based composition according to any one of the above <1> to <33>, wherein the water-based composition can further contain one or more members selected from the group consisting of clay minerals, disintegration inhibitors, specific gravity conditioners, water-soluble polymers, ultraviolet protective agents, moisturizing agents, defoaming agents, dispersants, alcohols, surfactants, anticorrosive agents, antioxidants, chelating agents, and pH adjustment agents, and wherein the water-based composition contains a liquid medium containing at least 10% by mass of water in an amount of preferably 30% by mass or more, more preferably 40% by mass or more, even more preferably 50% by mass or more, even more preferably 70% by mass or more, even more preferably 80% by mass or more, and even more preferably 90% by mass or more, and preferably 99.7% by mass or less.

<35> The water-based composition according to any one of the above <1> to <34>, wherein in the water-based composition, the content of the above component (A) is preferably 0.3% by mass or more, and more preferably 0.4% by mass or more, and preferably 5% by mass or less, more preferably 3% by mass or less, even more preferably 1% by mass or less, and still even more preferably 0.7% by mass or less, and the content of the above component (B) is preferably 0.02% by mass or more, more preferably 0.05% by mass or more, even more preferably 0.07% by mass or more, and still even more preferably 0.09% by mass or more, and preferably 1% by mass or less, more preferably 0.5% by mass or less, even more preferably 0.3% by mass or less, even more preferably 0.2% by mass or less, and still even more preferably 0.15% by mass or less.

<36> The water-based composition according to any one of the above <1> to <35>, wherein the content of the above component (B), based on 100 parts by mass of the component (A), is preferably 5 parts by mass or more, more preferably 10 parts by mass or more, and even more preferably 15 parts by mass or more, and preferably 100 parts by mass or less, more preferably 50 parts by mass or less, even more preferably 40 parts by mass or less, and still even more preferably 30 parts by mass or less.

<37> The water-based composition according to any one of the above <1> to <36>, wherein a viscosity at 80° C. and a rotational speed of 30 rpm is preferably 90 mPa·s or more, more preferably 100 mPa·s or more, and even more preferably 120 mPa·s or more, and preferably 100,000 mPa·s or less, more preferably 50,000 mPa·s or less, even more preferably 30,000 mPa·s or less, and still even more preferably 10,000 mPa·s or less.

<38> The water-based composition according to any one of the above <1> to <37>, wherein a ratio of a viscosity at 80° C. to a viscosity at 25° C. (80° C./25° C.) at a rotational speed of 30 rpm is preferably from 0.6 to 3.5, more preferably from 0.7 to 2.0, and even more preferably from 0.8 to 1.5.

<39> The water-based composition according to any one of the above <1> to <38>, wherein a ratio of a viscosity at a rotational speed of 3 rpm to a viscosity at a rotational speed of 30 rpm (3 rpm/30 rpm) at a temperature of 25° C. is preferably 2 or more, more preferably 2.5 or more, and even more preferably 3 or more, and the upper limit thereof is 10 or so.

<40> Use of a water-based composition as defined in any one of the above <1>~<39>, as cosmetics such as cream, milky lotion, or lipstick.

<41> Use of a water-based composition as defined in any one of the above <1>~<39>, as household articles such as fragrance, shampoo, or hairdye.

<42> Use of a water-based composition as defined in any one of the above <1>~<39>, as industrially manufactured articles such as blowing agents, paints, and concrete.

<43> Use of a water-based composition as defined in any one of the above <1>~<39>, as any one of fluids selected from the group consisting of drilling fluids, spacer fluids, injection fluids for well stimulations, and displacement fluids for enhanced oil recovery, which can be suitably used in piling construction, underground extraction of petroleum or the like, or well drilling of oil fields.

<44> A method for treating an underground layer characterized in that the method includes treating an underground layer with a water-based composition as defined in any one of the above <1> to <45>.

<45> The method according to the above <44>, characterized in that a natural gas or a crude oil in the underground layer is extracted by using a water-based composition as defined in the above <1> to <45> as any one of fluids selected from the group consisting of drilling fluids, spacer fluids, injection fluids for well stimulations, and displacement fluids for enhanced oil recovery.

<46> A method for recovering earth and sand or rocks generated by drilling, including feeding a water-based composition as defined in any one of the above <1> to <45> to a tip end of an underground drilling hole, and recovering earth and sand or rocks generated by drilling aboveground.

<47> The method according to the above <46>, characterized in that a water-based composition as defined in any one of the above <1> to <45> is fed to a tip end of an underground drilling hole, to disperse earth and sand or rocks generated by drilling in the above water-based composition.

EXAMPLES

The present invention will be described more specifically by means of the following Examples and Comparative Examples, without intending to limit the scope of the present invention to the following Examples. As to chemicals used, ones manufactured by Wako Pure Chemicals Industries, Ltd. were used, unless specified otherwise.

[Number-Average Fiber Diameter of Fine Cellulose Fibers]

Water is added to fine cellulose fibers to provide a dispersion of which concentration is 0.0001% by mass. The dispersion is added dropwise to mica (mica), and dried to provide an observation sample. A fiber height of the cellulose fibers in the observation sample is measured with an atomic force microscope AFM, Nanoscope III Tapping mode AFM, manufactured by Digital Instrument, a probe used being Point Probe (NCH) manufactured by NANOSENSORS. During that measurement, five or more sets of fine cellulose fibers are extracted from a microscopic image in which the cellulose fibers can be confirmed, and a number-average fiber diameter is calculated from those fiber heights.

[Carboxy Group Contents of Fine Cellulose Fibers and Fine Cellulose Fiber Composite]

Fine cellulose fibers or a fine cellulose fiber composite with the mass of 0.5 g on a dry basis is placed in a 100 mL beaker, ion-exchanged water or a mixed solvent of methanol/water=2/1 is added thereto to make up a total volume of 55 mL. Five milliliters of a 0.01 M aqueous sodium chloride solution is added thereto to provide a dispersion, and the dispersion is stirred until the fine cellulose fibers or the fine cellulose fiber composite is sufficiently dispersed. A 0.1 M hydrochloric acid is added to this dispersion to adjust its pH to 2.5 to 3, and a 0.05 M aqueous sodium hydroxide solution is added dropwise to the dispersion with an automated titration instrument manufactured by DKK-TOA CORPORATION under the trade name of "AUT-50," under the conditions of a waiting time of 60 seconds. The values of electroconductivity and a pH are measured every minute, and the measurements are continued up to a pH of 11 or so to obtain an electroconductivity curve. A titrated amount of sodium hydroxide is obtained from this electroconductivity curve, and the carboxy group content of the fine cellulose fibers or the fine cellulose fiber composite is calculated in accordance with the following formulas:

Carboxy Group Content (mmol/g)=Titrated Amount of Sodium Hydroxide×Aqueous Sodium Hydroxide Solution Concentration (0.05 M)/Mass of Cellulose Fibers (0.5 g)

Preparation Example 1 of Fine Cellulose Fibers—Dispersion of Carboxy Group-Containing Fine Cellulose Fibers Obtained by Treating Natural Cellulose with N-Oxyl Compound Needle-leaf bleached kraft pulp manufactured by Fletcher Challenge Canada Ltd., under the trade name of "Machenzie," CSF 650 ml, was used as natural cellulose fibers. As TEMPO, a commercially available product manufactured by ALDRICH, Free radical, 98% by mass, was used. As sodium hypochlorite, a commercially available product manufactured by Wako Pure Chemical Industries, Ltd. was used. As sodium bromide, a commercially available product manufactured by Wako Pure Chemical Industries, Ltd. was used.

First, 100 g of the needle-leaf bleached kraft pulp fibers were sufficiently stirred in 9,900 g of ion-exchanged water, and 1.25% by mass of TEMPO, 12.5% by mass of sodium bromide, and 28.4% by mass of sodium hypochlorite were added in this order to 100 g of the mass of the pulp. Using a pH stud, a 0.5 M sodium hydroxide was added dropwise to keep a pH at 10.5. After the reaction was carried out at 20° C. for 120 minutes, the dropwise addition of sodium hydroxide was stopped, to provide oxidized pulp. The oxidized pulp obtained was sufficiently washed with ion-exchanged water, and subsequently subjected to a dehydration treatment. Thereafter, 3.9 g of the oxidized pulp and 296.1 g of ion-exchanged water were subjected twice to a finely pulverizing treatment with a high-pressure homogenizer manufactured by Sugino Machine Limited, Starburstlabo HJP-2 5005 at 245 MPa, to provide a dispersion of carboxy group-containing fine cellulose fibers, a solid content concentration of which was 1.3% by mass. These fine cellulose fibers had a number-average fiber diameter of 3.3 nm, a carboxy group content of 1.8 mmol/g, and an aspect ratio of 320, and a crystallinity of 57%. Here, in the table given later, the resulting carboxy group-containing fine cellulose fibers are listed as Na-form fine cellulose fibers, Na-Form CSNF.

Preparation Example 2 of Fine Cellulose Fibers—Dispersion of H-Form Carboxy Group-Containing Fine Cellulose Fibers Obtained by Acidic Treatment In a beaker, 4,085 g of ion-exchanged water was added to 4,088.75 g of a dispersion of carboxy group-containing fine cellulose fibers obtained in Preparation Example 1, a solid content concentration of which was 1.3% by mass, to provide a 0.5% by mass aqueous solution, and the aqueous solution was stirred with a mechanical stirrer at room temperature, 25° C., for 30 minutes. Next, the beaker was charged with 245 g of a 1 M aqueous hydrochloric acid solution, and the contents were allowed to react for 1 hour at room temperature. After the termination of the reaction, the reaction mixture was filtered and washed with a large amount of ion-exchanged water, to remove hydrochloric acid and salt, to provide a dispersion of H-form carboxy group-containing fine cellulose fibers, a solid content concentration of which was 0.5% by mass. The resulting fine cellulose fibers had a number-average fiber diameter of 3.3 nm, and a carboxy group content of 1.8 mmol/g, and an aspect ratio and a crystallinity which were the same as the carboxy group-containing fine cellulose fibers obtained in Preparation Example 1. Here, in the table given later, the resulting carboxy group-containing fine cellulose fibers are listed as H-form fine cellulose fibers, H-Form CSNF.

Examples 1 to 24 and Comparative Examples 1 to 10

In a 120 mL standard bottle No. 11, manufactured by AS ONE Corporation, 61.5 g of ion-exchanged water was supplied to a dispersion of carboxy group-containing fine cellulose fibers listed in Table 1 or 2, a solid content concentration of which was 1.3% by mass, and the mixture was subjected to an ultrasonication homogenizer treatment US-300E manufactured by NIHONSEIKI KAISHA, LTD. at an output of 300 W, 3 repeated runs of a 40-second treatment, to prepare a homogenously mixed dispersion of carboxy group-containing fine cellulose fibers, a solid content concentration of which was as listed in Table 1 or 2. To the dispersion obtained, the component (B) of the kinds as listed in Table 1 or 2 was added in an amount as listed in Table 1 or 2, based on 100 parts by mass of the carboxy group-containing fine cellulose fibers, and the mixture was stirred at room temperature with a magnetic stirrer for 3 hours, and then allowed to stand at room temperature overnight, to provide a water-based composition. The composition obtained was allowed to stand in water controlled to 25° C. for 5 hours, and then subjected to a viscosity measurement within 2 minutes with a B-type viscometer, Model TVB10 viscometer manufactured by TOKI SANGYO CO., LTD., with rotors M1: measured viscosity≤100 mPa·s, M2: measured viscosity≤500 mPa·s, M3: measured viscosity≤2,000 mPa·s, M4: measured viscosity >2,000 mPa·s being properly applied, at a rotational speed of 30 rpm and a measurement time of 60 seconds. Thereafter, the mixture was allowed to stand in an oven at 80° C. for 5 hours, and then taken out, and again subjected to a viscosity measurement under the same conditions as above. The measured viscosity at 80° C. (mPa·s) and a ratio of a measured viscosity at 80° C. to a measured viscosity at 25° C. (η80° C./η25° C.) are shown in Tables 1 and 2.

Comparative Example 11

The treatments were carried out in the same manner as in Example 3 except that an aqueous solution of guar gum GRINSTED GUAR175, Guar, manufactured by SANSHO Co., Ltd., a solid content concentration of which was 0.5% by mass, was used in place of the dispersion of carboxy group-containing fine cellulose fibers. The results are shown in Table 2.

Comparative Example 12

The treatments were carried out in the same manner as in Example 3 except that an aqueous solution of carboxymethyl cellulose F350HC, an Na-Form CMC, a solid content concentration of which was 0.5% by mass, manufactured by NIPPON PAPER INDUSTRIES CO., LTD. was utilized, in place of the dispersion of carboxy group-containing fine cellulose fibers. The results are shown in Table 2.

Reference Example 1

An aqueous solution of guar gum GRINSTED GUAR175, Guar, manufactured by SANSHO Co., Ltd., a solid content concentration was 0.5% by mass was evaluated in the same manner as in Example 1. The results are shown in Table 2.

Reference Example 2

An aqueous solution of carboxymethyl cellulose F350HC, an Na-Form CMC, a solid content concentration of which was 0.5% by mass was evaluated in the same manner as in Example 1. The results are shown in Table 2.

Of the additives listed in Tables 1 and 2, those other than ones manufactured by Wako Pure Chemical Industries, Ltd. are as follows.

*1 Trioxypropylenediamine: JEFFAMINE D-230, manufactured by MITSUI FINE CHEMICALS;
*2 Hexoxypropylenediamine: JEFFAMINE D-400, manufactured by MITSUI FINE CHEMICALS;
*3 Pentoxypropylenetriamine: JEFFAMINE T-403, manufactured by MITSUI FINE CHEMICALS;
*4 Tri-tertiary amine glycol: Kaolizer P-200, manufactured by Kao Corporation;
*5 Polyoxypropylenediamine: JEFFAMINE D-2000, manufactured by MITSUI FINE CHEMICALS, average 33mer
*6 Polyoxyethylene propyleneamine: JEFFAMINE M-2070, manufactured by MITSUI FINE CHEMICALS, average 42mer

TABLE 1

| | Component (A) | | Component (B) | | | |
|---|---|---|---|---|---|---|
| | Kinds | Content in Composition, % by mass | Kinds | General Formula No. | No. of Carbon Atoms per Molecule | No. of Nitrogen Atoms per Molecule |
| Ex. 1 | Na-Form CSNF | 0.5 | Myristylbenzyldimethylammonium chloride | (1) | 23 | 1 |
| Ex. 2 | Na-Form CSNF | 0.5 | Myristylbenzyldimethylammonium chloride | (1) | 23 | 1 |
| Ex. 3 | Na-Form CSNF | 0.5 | Myristylbenzyldimethylammonium chloride | (1) | 23 | 1 |
| Ex. 4 | Na-Form CSNF | 0.5 | Myristylbenzyldimethylammonium chloride | (1) | 23 | 1 |
| Ex. 5 | Na-Form CSNF | 0.5 | Myristylbenzyldimethylammonium chloride | (1) | 23 | 1 |
| Ex. 6 | Na-Form CSNF | 0.3 | Myristylbenzyldimethylammonium chloride | (1) | 23 | 1 |
| Ex. 7 | Na-Form CSNF | 1.0 | Myristylbenzyldimethylammonium chloride | (1) | 23 | 1 |
| Ex. 8 | Na-Form CSNF | 0.5 | Tetramethylammonium bromide | (1) | 4 | 1 |
| Ex. 9 | Na-Form CSNF | 0.5 | Tetraethylammonium bromide | (1) | 8 | 1 |
| Ex. 10 | Na-Form CSNF | 0.5 | Hexyltrimethylammonium bromide | (1) | 9 | 1 |
| Ex. 11 | Na-Form CSNF | 0.5 | Phenyltripropylammonium chloride | (1) | 15 | 1 |
| Ex. 12 | Na-Form CSNF | 0.5 | Hexylamine | (2) | 6 | 1 |
| Ex. 13 | Na-Form CSNF | 0.5 | Dipropylamine | (2) | 6 | 1 |
| Ex. 14 | Na-Form CSNF | 0.5 | Triethylamine | (2) | 6 | 1 |
| Ex. 15 | Na-Form CSNF | 0.5 | Dimethylaminohexanol | (2) | 8 | 1 |
| Ex. 16 | Na-Form CSNF | 0.5 | N,N-Dimethyl-4-aminopyridine | (2) | 8 | 2 |

TABLE 1-continued

| | | | | | | | |
|---|---|---|---|---|---|---|---|
| Ex. 17 | Na-Form CSNF | 0.5 | Trans-1,4-cyclohexanediamine | (3) | 6 | 2 | |
| Ex. 18 | Na-Form CSNF | 0.5 | N,N,N-Tetramethyl-1,6-hexanediamine | (3) | 10 | 2 | |
| Ex. 19 | Na-Form CSNF | 0.5 | Trioxypropylenediamine | (3) | 12 | 2 | |
| Ex. 20 | Na-Form CSNF | 0.5 | 1,12-Dodecanediamine | (3) | 12 | 2 | |
| Ex. 21 | Na-Form CSNF | 0.5 | Hexoxypropylenediamine | (3) | 21 | 2 | |

| | Component (B) | | | | Evaluation | |
|---|---|---|---|---|---|---|
| | Molecular Weight | No. of Carbon Atoms/ No. of Nitrogen Atoms | Content in Composition, % by mass | Content Based on 100 Parts by Mass of Component (A), Parts by Mass | Viscosity at 80° C., mPa·s | Ratio of Viscosities, 80° C./25° C. |
| Ex. 1 | 367 | 23 | 0.025 | 5 | 201 | 0.62 |
| Ex. 2 | 367 | 23 | 0.050 | 10 | 316 | 0.97 |
| Ex. 3 | 367 | 23 | 0.100 | 20 | 1,598 | 1.08 |
| Ex. 4 | 367 | 23 | 0.200 | 40 | 1,085 | 0.97 |
| Ex. 5 | 367 | 23 | 0.500 | 100 | 390 | 0.89 |
| Ex. 6 | 367 | 23 | 0.060 | 20 | 99 | 0.95 |
| Ex. 7 | 367 | 23 | 0.200 | 20 | 5,320 | 0.98 |
| Ex. 8 | 154 | 4 | 0.100 | 20 | 88 | 0.67 |
| Ex. 9 | 210 | 8 | 0.100 | 20 | 601 | 0.81 |
| Ex. 10 | 224 | 9 | 0.100 | 20 | 550 | 0.89 |
| Ex. 11 | 256 | 15 | 0.100 | 20 | 548 | 0.96 |
| Ex. 12 | 101 | 6 | 0.100 | 20 | 285 | 0.96 |
| Ex. 13 | 101 | 6 | 0.100 | 20 | 275 | 1.01 |
| Ex. 14 | 101 | 6 | 0.100 | 20 | 279 | 1.00 |
| Ex. 15 | 145 | 8 | 0.100 | 20 | 143 | 0.82 |
| Ex. 16 | 122 | 4 | 0.100 | 20 | 154 | 0.93 |
| Ex. 17 | 114 | 3 | 0.100 | 20 | 471 | 1.03 |
| Ex. 18 | 112 | 5 | 0.100 | 20 | 651 | 0.81 |
| Ex. 19 | 230 | 6 | 0.100 | 20 | 204 | 0.93 |
| Ex. 20 | 200 | 6 | 0.100 | 20 | 1,500 | 1.26 |
| Ex. 21 | 400 | 10.5 | 0.100 | 20 | 504 | 0.99 |

TABLE 2

| | Component (A) | | Component (B) | | | |
|---|---|---|---|---|---|---|
| | Kinds | Content in Composition, % by mass | Kinds | General Formula No. | No. of Carbon Atoms per Molecule | No. of Nitrogen Atoms per Molecule |
| Ex. 22 | Na-Form CSNF | 0.5 | Pentoxypropylenetriamine | (4) | 21 | 3 |
| Ex. 23 | Na-Form CSNF | 0.5 | Tri-tertiary amine glycol | (5) | 27 | 3 |
| Ex. 24 | Na-Form CSNF | 0.5 | Lauryldiethanolamide | (6) | 16 | 1 |
| Comp. Ex. 1 | Na-Form CSNF | 0.5 | None | — | — | — |
| Comp. Ex. 2 | Na-Form CSNF | 0.5 | Myristylbenzyldimethylammonium chloride | (1) | 23 | 1 |
| Comp. Ex. 3 | Na-Form CSNF | 0.1 | Myristylbenzyldimethylammonium chloride | (1) | 23 | 1 |
| Comp. Ex. 4 | Na-Form CSNF | 0.5 | Tetraethylene glycol | — | 8 | 0 |
| Comp. Ex. 5 | Na-Form CSNF | 0.5 | Ammonium sulfate | — | 0 | 1 |
| Comp. Ex. 6 | Na-Form CSNF | 0.5 | Ammonia | — | 0 | 1 |
| Comp. Ex. 7 | Na-Form CSNF | 0.5 | Ethylenediamine | (3) | 2 | 2 |
| Comp. Ex. 8 | Na-Form CSNF | 0.5 | Polyoxypropylenediamine | (3) | 99 | 2 |
| Comp. Ex. 9 | Na-Form CSNF | 0.5 | Polyoxyethylenediamine | (2) | 94 | 1 |
| Comp. Ex. 10 | H-Form CSNF | 0.5 | Triethylamine propyleneamine | (2) | 6 | 1 |
| Comp. Ex. 11 | Guar | 0.5 | Myristylbenzyldimethylammonium chloride | (1) | 23 | 1 |
| Comp. Ex. 12 | Na-Form CMC | 0.5 | Myristylbenzyldimethylammonium chloride | (1) | 23 | 1 |
| Ref. Ex. 1 | Guar | 0.5 | None | — | — | — |
| Ref. Ex. 2 | Na-Form CMC | 0.5 | None | — | — | — |

| | Component (B) | | | | Evaluation | |
|---|---|---|---|---|---|---|
| | Molecular Weight | No. of Carbon Atoms/ No. of Nitrogen Atoms | Content in Composition, % by mass | Content Based on 100 Parts by Mass of Component (A), Parts by Mass | Viscosity at 80° C., mPa·s | Ratio of Viscosities, 80° C./25° C. |
| Ex. 22 | 440 | 7 | 0.100 | 20 | 188 | 0.91 |
| Ex. 23 | 457 | 9 | 0.100 | 20 | 585 | 0.91 |

TABLE 2-continued

| | | | | | | |
|---|---|---|---|---|---|---|
| Ex. 24 | 287 | 16 | 0.100 | 20 | 192 | 3.43 |
| Comp. Ex. 1 | — | — | 0 | 0 | 47 | 0.24 |
| Comp. Ex. 2 | 367 | 23 | 1.000 | 200 | 10 | 0.27 |
| Comp. Ex. 3 | 367 | 23 | 0.020 | 20 | 2 | 0.71 |
| Comp. Ex. 4 | 194 | — | 0.100 | 20 | 30 | 0.16 |
| Comp. Ex. 5 | 132 | 0 | 0.100 | 20 | 70 | 0.60 |
| Comp. Ex. 6 | 17 | 0 | 0.100 | 20 | 15 | 0.63 |
| Comp. Ex. 7 | 60 | 1 | 0.100 | 20 | 11 | 0.07 |
| Comp. Ex. 8 | 2000 | 49.5 | 0.100 | 20 | 13 | 0.65 |
| Comp. Ex. 9 | 2000 | 94 | 0.100 | 20 | 18 | 0.13 |
| Comp. Ex. 10 | 101 | 6 | 0.100 | 20 | 32 | 0.33 |
| Comp. Ex. 11 | 367 | 23 | 0.100 | 20 | 64 | 0.26 |
| Comp. Ex. 12 | 367 | 23 | 0.100 | 20 | 43 | 0.23 |
| Ref. Ex. 1 | — | — | 0 | 0 | 49 | 0.29 |
| Ref. Ex. 2 | — | — | 0 | 0 | 77 | 0.29 |

From Tables 1 and 2, it was clarified that characteristic viscous compositions that did not reduce viscosity even under high-temperature conditions were obtained by adding a compound of which ratio of the number of carbon atoms to the number of nitrogen atom or atoms per molecule of the compound (number of carbon atoms/number of nitrogen atoms) is specified to a specified dispersion of carboxy group-containing fine cellulose fibers. On the other hand, Comparative Example 10 where carboxy group-containing fine cellulose fibers not forming a salt with an alkali metal were used did not exhibit the addition effects of the component (B), and its viscosity at a high temperature was low.

Specific formulations of the water-based compositions of the present invention will be exemplified hereinbelow.

Production Example 1: Cosmetics—Milky Lotion

The amount 1.5 g of stearyl alcohol, 1.5 g of cetyl alcohol, 2.0 g of stearic acid, 10 g of glycerol, 5 g of 1,3-butylene glycol, 1 g of Vaseline, 2 g of heavy liquid isoparaffin, 5 g of methyl polysiloxane, 0.6 g of perfume, and 71.4 g of a viscous water-based composition prepared in Example 3 are mixed while stirring according to a conventional method, whereby skin cosmetics can be suitably prepared. Since the resulting skin cosmetics have controlled lowering in viscosity at a high temperature, the skin cosmetics can be suitably used outdoor in summer seasons.

Production Example 2: Household Articles—Fragrance

Two grams of a perfume, a floral blend perfume, manufactured by Ogawa & Co., Ltd., and 38.5 g of a dispersion of carboxy group-containing fine cellulose fibers, a solid content concentration of which is 1.3% by mass are supplied into 61.3 g of ion-exchanged water, and the mixture is subjected to a ultrasonic homogenizer treatment in the same manner as in Example 1, to provide 100 g of a dispersion of carboxy group-containing fine cellulose fibers, a solid content concentration of which is 0.5% by mass, in which perfume is uniformly blended. To the dispersion obtained myristylbenzyldimethylammonium chloride is added such that the amount added is 20 parts by mass based on 100 parts by mass of the carboxy group-containing fine cellulose fibers, and the mixture is stirred with a magnetic stirrer at room temperature for 3 hours, and thereafter allowed to stand overnight, whereby a gel-like fragrance composition can be prepared. Since the resulting gel-like fragrance composition has controlled lowering in viscosity at a high temperature, the fragrance composition can be suitably used even under the environment of marked temperature changes in automobiles in the summer seasons.

Production Example 3: Industrially Manufactured Article—Paint

Forty-six grams of a viscous water-based composition prepared in Example 3 is mixed while stirring according to a conventional method with 20 g of titanium dioxide, 14 g of calcium carbonate, and 20 g of talc, whereby an aqueous pigment-dispersed paste can be prepared. Since the resulting aqueous pigment-dispersed paste has controlled lowering in viscosity at a high temperature, the aqueous pigment-dispersed paste can be suitably used even during the operation of pigment coating outdoors in the summer seasons.

Production Example 4: Drilling Mud Conditioner

Two grams of bentonite and 38.5 g of a dispersion of carboxy group-containing fine cellulose fibers, a solid content concentration of which is 1.3% by mass, are supplied into 61.3 g of ion-exchanged water, and the mixture is subjected to a ultrasonic homogenizer treatment in the same manner as in Example 1, to provide 100 g of a dispersion of carboxy group-containing fine cellulose fibers, a solid content concentration of which is 0.5% by mass, in which bentonite was uniformly blended. To the dispersion obtained myristylbenzyldimethylammonium chloride is added such that the amount added is 20 parts by mass based on 100 parts by mass of the carboxy group-containing fine cellulose fibers, and the mixture is stirred with a magnetic stirrer at room temperature for 3 hours, and thereafter allowed to stand overnight, whereby a drilling mud conditioner can be prepared. Since the resulting drilling mud conditioner has controlled lowering in viscosity at a high temperature, the drilling mud conditioner can be suitably used even under the high-temperature environment due to friction or geotherm during drilling.

<Use of Drilling Mud Conditioner>

By using a drilling mud conditioner prepared in the above Production Example 4 in the actual drilling step, a suitable viscosity is exhibited even under high-temperature conditions during drilling, whereby operability during drilling construction can be improved.

INDUSTRIAL APPLICABILITY

Since the fine cellulose fibers or a salt composite thereof of the present invention retains a high viscosity even under high temperatures, the fine cellulose fibers or a salt composite thereof can be suitably used in various industrial applications represented by thickening agents during gas and oil drilling, cosmetic applications, and other applications requiring manufactured article stability at high temperatures.

The invention claimed is:

1. A water-based composition comprising:
(A) fine cellulose fibers having a number-average fiber diameter of 0.5 nm or more and 200 nm or less, and having a carboxy group content of 0.1 mmol/g or more, wherein the carboxy group forms a salt with an alkali metal; and
(B) an additive comprising one or more compounds having carbon atoms and nitrogen atom or atoms, wherein a ratio thereof per molecule of the compound (number of carbon atoms/number of nitrogen atoms) is 3 or more and 45 or less,
wherein component (B) comprises one or more members selected from the group consisting of compounds represented by the following general formulas (1) to (6):

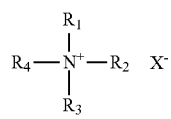
(1)

wherein each of $R_1$, $R_2$, $R_3$, and $R_4$, which may be identical or different, is an alkyl group having from 1 to 20 carbon atoms, an aryl group having from 6 to 20 carbon atoms, or an aralkyl group having from 7 to 20 carbon atoms; and X is F, Br, Cl, or I;

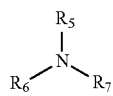
(2)

wherein each of $R_5$, $R_6$, and $R_7$, which may be identical or different, is a hydrogen atom, an alkyl group or a hydroxyalkyl group each having from 1 to 10 carbon atoms, an aryl group having from 6 to 20 carbon atoms, an aralkyl group having from 7 to 20 carbon atoms, or a heteroaromatic ring group;

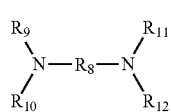
(3)

wherein $R_8$ is a (cyclo)alkylene group having from 3 to 18 carbon atoms or a polyoxyalkylene group having from 3 to 24 carbon atoms; and each of $R_9$, $R_{10}$, $R_{11}$, and $R_{12}$, which may be identical or different, is a hydrogen atom or a methyl group;

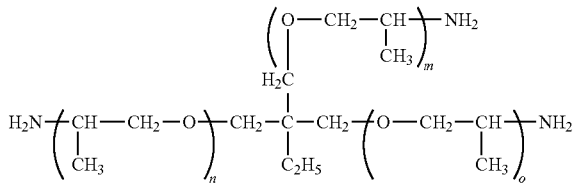
(4)

wherein each of m, n, and o is independently an average number of moles added of an oxypropylene group, wherein m+n+o is a number satisfying 1 or more and 12 or less;

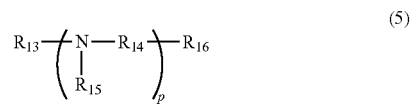
(5)

wherein $R_{13}$ is a hydrogen atom, a hydroxy group, or an alkyl group or a hydroxyalkyl group each having from 1 to 10 carbon atoms; $R_{14}$ is an alkylene group having from 1 to 8 carbon atoms; $R_{15}$ is a hydrogen atom, a hydroxy group, or an alkyl group or a hydroxyalkyl group each having from 1 to 6 carbon atoms; $R_{16}$ is a hydrogen atom or a hydroxy group; and p is from 1 to 6; and

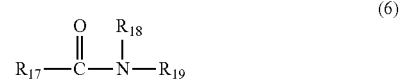
(6)

wherein $R_{17}$ is an alkyl group having from 6 to 18 carbon atoms; and each of $R_{18}$ and $R_{19}$, which may be identical or different, is a hydrogen atom or an alkyl group or a hydroxyalkyl group each having from 1 to 8 carbon atoms,
wherein the content of the component (A) is 0.2% by mass or more and 10% by mass or less and the content of the component (B) in the water-based composition is 0.02% by mass or more and 1% by mass or less,
wherein the content of the component (B) is 15 parts by mass or more and 150 parts by mass or less, based on 100 parts by mass of the component (A), and
wherein the water-based composition has a viscosity at 80° C. at a rotational speed of 30 rpm of 80 mPa·s or more.

2. The water-based composition according to claim 1, wherein the fine cellulose fibers are obtained by a method comprising oxidizing natural cellulose fibers in the presence of an N-oxyl compound.

3. The water-based composition according to claim 1, wherein the fine cellulose fibers have a carboxy group content of 0.1 mmol/g or more and 3.0 mmol/g or less.

4. The water-based composition according to claim 1, wherein the fine cellulose fibers have a carboxy group content of 0.4 mmol/g or more and 2.0 mmol/g or less.

5. The water-based composition according to claim 1, wherein a salt of the alkali metal in the fine cellulose fiber is one or more salts selected from the group consisting of Li, Na, K, and Rb.

6. The water-based composition according to claim 1, wherein the fine cellulose fibers are obtainable by a method comprising oxidizing natural cellulose fibers in the presence of an N-oxyl compound, to provide an alkali metal salt form of carboxy group-containing cellulose fibers (oxidization treatment step); and subjecting the resulting fibers to a finely pulverizing treatment (finely pulverizing step).

7. The water-based composition according to claim 1, wherein the component (B) comprises one or more members selected from the group consisting of quaternary ammonium salts, amines, and amides.

8. The water-based composition according to claim 1, wherein the component (B) comprises a quaternary ammonium salt.

9. The water-based composition according to claim 1, wherein the component (B) comprises a quaternary ammonium salt, and wherein the quaternary ammonium salt has a ratio of carbon atoms to nitrogen atom or atoms per molecule of the compound (number of carbon atoms/number of nitrogen atoms) of 4 or more and 30 or less.

10. The water-based composition according to claim 1, further comprising a liquid medium comprising at least 10% by mass of water.

11. The water-based composition according to claim 1, further comprising a liquid medium comprising at least 10% by mass of water, and wherein the content of the liquid medium in the water-based composition is 50% by mass or more.

12. The water-based composition according to claim 1, further comprising a liquid medium comprising at least 10% by mass of water, and wherein the content of the liquid medium in the water-based composition is 90% by mass or more.

13. The water-based composition according to claim 1, wherein the content of the component (A) in the water-based composition is 0.3% by mass or more and 5% by mass or less.

14. The water-based composition according to claim 1, wherein the content of the component (A) in the water-based composition is 0.3% by mass or more and 3% by mass or less.

15. A cosmetic selected from a cream, milky lotion, and lipstick, wherein said cosmetic comprises the water composition of claim 1.

16. A household article selected from aromatics, shampoos, and hairdyes, wherein said household article comprises the water composition of claim 1.

17. An industrially manufactured article selected from a blowing agent, paint, and concrete, wherein said industrially manufactured article comprises the water composition of claim 1.

18. A fluid selected from the group consisting of a drilling fluid, spacer fluid, injection fluid for well stimulations, and displacement fluid for enhanced oil recovery, which are usable during piling construction, extraction of petroleum, or well drilling in oil fields, wherein said fluid comprises the water composition of claim 1.

* * * * *